United States Patent
Si et al.

(10) Patent No.: US 11,726,072 B2
(45) Date of Patent: Aug. 15, 2023

(54) METHOD OF MOBILE MONITORING AND DETERMINING REQUISITE NUMBER OF MOBILE MONITORING VEHICLES

(71) Applicant: NOVA FITNESS CO., LTD., Jinan (CN)

(72) Inventors: Shuchun Si, Jinan (CN); Shanwen Liu, Jinan (CN); Shitian Kou, Jinan (CN)

(73) Assignee: NOVA FITNESS CO., LTD., Jinan (CN)

( * ) Notice: Subject to any disclaimer, the term of this patent is extended or adjusted under 35 U.S.C. 154(b) by 265 days.

(21) Appl. No.: 17/156,669

(22) Filed: Jan. 25, 2021

(65) Prior Publication Data
US 2021/0172917 A1 Jun. 10, 2021

Related U.S. Application Data

(63) Continuation-in-part of application No. PCT/CN2019/074042, filed on Jan. 31, 2019.

(30) Foreign Application Priority Data

Jul. 25, 2018 (WO) .................. PCT/IB2018/055525
Jul. 25, 2018 (WO) .................. PCT/IB2018/055531

(51) Int. Cl.
*G01N 33/00* (2006.01)
*G08G 1/00* (2006.01)
(Continued)

(52) U.S. Cl.
CPC ....... *G01N 33/0062* (2013.01); *G01N 33/007* (2013.01); *G01N 33/0031* (2013.01);
(Continued)

(58) Field of Classification Search
CPC ............ G01N 33/0075; G01N 33/007; G01N 33/0031; G01N 33/0062; G08G 1/20
See application file for complete search history.

(56) References Cited

U.S. PATENT DOCUMENTS 8,325,061 B2 * 12/2012 Groves .............. G01N 33/0075
340/901
2011/0163892 A1 * 7/2011 Groves .............. G01N 33/0075
340/901
(Continued)

FOREIGN PATENT DOCUMENTS

EP 2199790 A1 * 6/2010 ................ G01J 3/02
EP 3629261 A1 * 4/2020

*Primary Examiner* — Nathaniel J Kolb
(74) *Attorney, Agent, or Firm* — Matthias Scholl P.C.; Matthias Scholl

(57) ABSTRACT

A method for determining a false negative rate of mobile monitoring and requisite number of mobile monitoring vehicles. The method focuses on road network of an urban area, by installing air pollution detection equipment on the mobile monitoring vehicles, to monitor air quality of the urban area. The method includes establishing a curve model of monitoring times for the mobile monitoring vehicles, determining two parameters of expected indicator: covered range, number of scheduled detections; and finding out a requisite number ($C_0$) of the mobile monitoring vehicles, corresponding to a curve model which meets the two parameters of expected indicator.

10 Claims, 13 Drawing Sheets

(51) Int. Cl.
   *G06Q 30/018* (2023.01)
   *G06Q 50/26* (2012.01)
   *G07C 5/00* (2006.01)
   *G08G 1/01* (2006.01)
   *G08G 1/127* (2006.01)

(52) U.S. Cl.
   CPC ........... *G01N 33/0075* (2013.01); *G08G 1/20* (2013.01); *G01N 33/004* (2013.01); *G01N 33/0037* (2013.01); *G01N 33/0039* (2013.01); *G01N 33/0047* (2013.01); *G06Q 30/018* (2013.01); *G06Q 50/26* (2013.01); *G07C 5/008* (2013.01); *G08G 1/0112* (2013.01); *G08G 1/0137* (2013.01); *G08G 1/127* (2013.01)

(56) References Cited

U.S. PATENT DOCUMENTS

2017/0108350 A1\* 4/2017 Nagao ................ G01D 3/08
2018/0136180 A1\* 5/2018 Chou ................ G01N 33/0036

\* cited by examiner

| | |
|---|---|
|  RSU with 40+ detections |  RSU with 10~20 detections |
|  RSU with 30~40 detections |  RSU with 1~10 detections |
|  RSU with 20~30 detections |  RSU with no detection |

METHOD OF MOBILE MONITORING AND DETERMINING REQUISITE NUMBER OF MOBILE MONITORING VEHICLES

CROSS-REFERENCE TO RELAYED APPLICATIONS

This application is a continuation-in-part of International Patent Application No. PCT/CN2019/074042 with an international filing date of Jan. 31, 2019, designating the United States, now pending, and further claims foreign priority benefits to International Patent Application No. PCT/IB2018/055525 filed on Jul. 25, 2018, and to International Patent Application No. PCT/IB2018/055531 filed on Jul. 25, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a method for determining mobile monitoring undetected rate and rated number of mobile monitoring vehicles (MMVs) and belongs to technical field of environmental monitoring.

Atmospheric environmental monitoring is the process of measuring the types and concentrations of pollutants in the atmosphere and observing their temporal and spatial distribution and changes. The main pollutants monitored are sulfur dioxide, nitrogen oxides, ozone, carbon monoxide, $PM_1$, $PM_{2.5}$, $PM_{10}$, $PM_{100}$ and VOCs (volatile organic compounds) or TVOC (total volatile organic compounds). The atmospheric environmental monitoring system can collect and process the monitored data, and timely and accurately reflect the regional ambient air quality status and changes. Environmental protection departments can use these data for environmental decision-making, environmental management, and pollution prevention; the public can take personal protection and rationally arrange their lives based on environmental data.

The current atmospheric environment monitoring equipment mainly includes fixed monitoring stations and mobile monitoring equipment. The current fixed monitoring stations are mainly divided into large fixed monitoring stations (large stations) and small monitoring stations (small stations). Mobile monitoring equipment mainly comprises special atmospheric environmental monitoring vehicles, drones and handheld devices.

The large fixed monitoring site is equivalent to an independent laboratory, which monitors and analyzes the levels of multiple pollutants in the environment through expensive and sophisticated instruments. It has characterized by a variety of pollutants and high accuracy. However, the general investment of large fixed monitoring stations is in the millions to ten million level, which requires high financial support. Therefore, the number of large fixed monitoring sites is relatively small and cannot be rolled out on a large scale, and only representative and feasible location can be selected for construction. At the same time, large fixed monitoring sites also have high requirements for site selection. The site needs a large area to accommodate large equipment, and equipment needs temperature and humidity control. A large number of professional and high-quality personnel would be required to use the instrument, analyze data, and maintain the instrument. In addition, the data obtained from super stations can only be inferred at a single point, and it is difficult to find other nearby super stations to verify.

Small monitoring sites integrate grids and batches to reduce costs by integrating low-cost, miniaturized sensors. This also has the advantages of convenient power consumption (can be powered by solar power) and easy installation. However, the accuracy and consistency of monitoring data of small stations need to be improved, and sufficient operational guarantee is needed. Although a small monitoring site covers a wide area, it is still a fixed monitoring with limited flexibility.

The special atmospheric environment monitoring vehicle is a vehicle equipped with a sampling system, pollutant monitoring instruments, meteorological parameter observers, data processing devices and other auxiliary equipment. It is a mobile monitoring station and a supplement to the fixed ground monitoring stations. The atmospheric environmental monitoring vehicle can be driven to the scene of a pollution accident or a suspicious point to take measurements at any time, in order to grasp the pollution situation in time, and its use is not restricted by time, place and season. But it needs to be driven by full-time personnel, and professional personnel are required to operate related instruments. It is expensive and cannot be used on a large scale.

UAV air pollution monitoring is a method of monitoring the atmospheric environment by using a drone equipped with a miniaturized atmospheric monitoring device. It can realize three-dimensional monitoring of air pollution in vertical sections at high altitudes, with a wide monitoring range and high monitoring efficiency. However, high airflow may be disturbed, and drone propellers may also cause airflow disturbances, which may affect the monitoring results. At the same time, there are some problems with the current drone's endurance, which also hinders continuous monitoring. Using drones to monitor air pollution also requires professional operations.

In the existing monitoring methods, for example, large-scale stations and special mobile monitoring vehicles use the weighing method, micro-oscillation balance method, and β-ray method to measure particulate matter. GC-FID (Gas Chromatography-Flame Ion Detection) is used for VOCs detection. Most of these precision testing instruments are large and expensive, which is not convenient for extensive spot monitoring. The detection of other pollutants such as sulfur dioxide, nitrogen oxides, ozone and carbon monoxide have similar problems. The special mobile monitoring vehicles need to park to monitor the air pollutants when they reach the designated location, which is equivalent to a fixed monitoring station and cannot be moved in real time for monitoring.

The urban gridded air pollutant monitoring and measurement investment is costly, and current monitoring methods cannot achieve comprehensive coverage. Each monitoring point requires professional installation and maintenance, and the corresponding calibration needs to be performed at intervals. The sampling port of each monitoring point is generally installed at a position which is at least three meters high with respect to the ground, which is not conducive to monitoring ground pollution (such as road dust). At the same time, roads and areas with high population density often have dense traffic flows, especially taxis, such locations require intensive and focused monitoring.

Using urban social vehicles as mobile monitoring vehicles, equipped with atmospheric pollutant monitoring equipment and positioning equipment, combined with wireless transmission technology, can achieve large-scale near-field monitoring of air pollution.

Fixed-point monitoring features

First of all, covered range is fixed for fixed-point monitoring. The data at the monitoring point can only represent the pollution situation near the monitoring point, and the pollution situation far away from the monitoring point can only be indirectly estimated, the areas between the monitoring points are missing areas.

This kind of area is covered by discrete monitoring points. The number of these monitoring points depends on the pollution range that each monitoring point can effectively represent.

FIG. 2 shows the limitations of fixed grid layout.

Mobile Monitoring Features

The distinctive feature of mobile monitoring is that the mobile device continuously changes with the movement of the moving vehicle. Its moving path is a traffic route and basically only monitors the area along the traffic network. So, its covered range area is the traffic network in the entire area.

Different Covered Range

1) Fixed monitoring: The monitoring area of each monitoring device is fixed and discrete "points";

2) Mobile monitoring: The monitoring area of each monitoring device is the entire road network, which is a continuous "line" or "belt";

3) "Line" coverage has significant advantages compared with "point" coverage

4) The larger range of data distribution obtained by the "line" coverage is more representative for the overall air pollution judgment of a city.

Monitoring Data From Different Sources

For the fixed monitoring mode, the data of each monitored location comes from the same or the same group of monitoring equipment;

For mobile monitoring mode, the data of each monitored location comes from many different monitoring devices.

In other words, the pollution situation at a certain location within the road network can be measured multiple times by different mobile devices (carried on mobile vehicles) at different time periods. In this way, the reliability of the data of the monitoring equipment can be indirectly evaluated through the correlation between the monitoring data of different equipment.

SUMMARY

Aiming at the lack of monitoring methods in the background technology and the characteristics of urban atmospheric environmental pollution monitoring, the disclosure provides a method for determining the missed detection rate of mobile monitoring based on the urban air pollutant monitoring data.

The disclosure utilizes a large number of randomly running social vehicles equipped with hidden installation monitoring equipment as a mobile monitoring vehicle and is assisted by fixed monitoring equipment, which can realize the real-time monitoring of the distribution and change of pollutants in urban areas. As long as the mobile monitoring equipment reaches a certain quantity, the monitoring data generated by these mobile devices can objectively reflect the true situation of urban air pollution distribution and pollution level.

Environmental monitoring needs to ensure that the monitoring data are objective and effective. Compared with other types of pollution, environmental pollution, especially atmospheric environmental pollution, has the characteristics of great changes with time and space. Monitoring based on these characteristics is of great significance for obtaining monitoring results that accurately reflect the actual state of atmospheric pollution. The spatial and temporal distribution of air pollutants and their concentrations are closely related to the distribution of pollutant emission sources, emissions, and topography, geomorphology, and meteorological conditions. Different types, properties and emission rules of pollutants will affect the spatial and temporal distribution of pollutants, and the level of atmospheric pollutants in the same place also fluctuates rapidly. There is a concept of time resolution in air pollution monitoring, which requires changes in pollutant concentration to be reflected within a specified time. For example, some acutely hazardous pollutants require a resolution of 3 minutes; some chemical aerosols, such as ozone, require a resolution of 10 minutes for the stimulation of the respiratory tract.

In order to better complete the monitoring of the air pollutant and reflect the real situation of urban pollutants, the disclosure realizes from fixed point monitoring to the whole road network monitoring and extensive geographical coverage by deploying a large number of various air pollutant monitoring devices on mobile monitoring vehicles and transmitting location and monitoring data in real time.

FIG. 1 shows the system composition of the disclosure. The system comprises a mobile monitoring vehicle equipped with monitoring equipment, a monitoring center, and a fixed monitoring station. The disclosure proposes to reasonably increase the density of equipment to achieve the coverage of motor vehicle roads in urban areas. At the same time, the monitoring equipment needs to transmit data in seconds in real time. Through multi-vehicle relay, 24-hour continuous monitoring can be realized, and finally reliable, objective and effective atmospheric environmental data is processed by the monitoring center. Extensive use of monitoring equipment makes up for the shortage of the number of points at each fixed monitoring site and provides data support for grid-based supervision.

The mobile monitoring vehicle equipped with online monitoring equipment for atmospheric pollutants is constantly moving in the city, and the concentration of pollutants, watering and road damage in all corners can be monitored in real time, so that atmospheric pollution monitoring can cover every community and every road section, avoiding dead spots and blind spots. At the same time, the system can also access data from fixed monitoring sites, making monitoring data more complete.

When the number of mobile vehicles equipped with on-line monitoring of atmospheric pollutants is small, the amount of collected monitoring data will be insufficient, and there will be no way to provide comprehensive information of urban pollutants in time without sufficient samples. When a certain number of monitoring vehicles equipped with a variety of pollutant monitoring equipment reach a certain number, it can avoid a large number of small-scale short-term air pollution missed detections, and can obtain more complete spatial and temporal coverage of pollutants, improving the effectiveness of monitoring data.

FIG. 6 shows the change in the concentration of pollutants at the same place over time. $T_0$ to $T_6$ indicate the time from appearance to disappearance of pollution and the corresponding concentration of pollutant at time $T3$ is the largest. Because air pollution changes rapidly with time, when there are not enough vehicles equipped with on-line monitoring equipment for atmospheric pollutants, the data between $T_0$ and $T_6$ at the same location may not be monitored. In this way, the actual pollution situation here cannot be obtained, and only as much as possible the data captured between $T_0$ and $T_6$ can reflect the full picture of real pollution. This solution proposes the use of a large number of mobile monitoring vehicles equipped with atmospheric pollutant monitoring equipment for data collection, which can capture most of the short-term pollution in a small area, can trace the source of the pollution, can analyze the causes of atmospheric pollution, and can provide objective and truthful information on air pollution for departmental law enforcement and public personal protection.

The installation density of equipment is greatly increased to realize the coverage of motor vehicle roads in urban areas. At the same time, the monitoring equipment needs to transmit data in seconds in real time. Through multi-vehicle relay, continuous monitoring can be achieved for 24 hours. The extensive use of monitoring equipment makes up for the lack of fixed monitoring points at each monitoring station and provides data support for grid-based supervision. A large number of mobile monitoring vehicles equipped with on-board air pollutants online monitoring systems is constantly moving in the city, and the pollutant concentration, watering and road damage in all corners can be monitored in real time, so that air pollution monitoring can cover every community, every road section and avoids dead ends and blind spots.

This plan proposes a model of the required number of mobile monitoring vehicles equipped with on-line monitoring equipment for atmospheric pollutants, and the specific number is determined based on the average undetected rate of monitoring. The average undetected rate represents the probability of detecting air pollution in a monitored area.

Method 1: Measured by the density of monitored vehicles per square kilometer

The method still looks at the number of monitoring devices relative to the density of an area.

As shown in FIG. 7, the average undetected rate is related to the density of monitoring equipment in cities, which is expressed as the number of vehicles per square kilometer. When the total number of vehicles dropped is small, the average number per square kilometer in the city will be small. The average undetected rate for pollutants that dissipate quickly in a small area will be very high. The higher the dropped density, the lower the average undetected rate. When the number of monitoring devices released reaches a certain value, such as when the delivery density reaches no, the average undetected rate will decrease to mo.

In order to ensure the objectivity of a city's air pollution monitoring data, a set of the highest average undetected rate index $M_0$ needs to be set. Correspondingly, a set of the lowest delivery density index $N_0$ can be measured. The higher the average undetected rate, the worse the objectivity of the monitoring data, so we expect to reduce the average undetected rate. In general, the average undetected rate of air pollutants to be monitored should be controlled below 50%. In terms of cost, it is reasonable to control the actual average undetected rate between 20% and 50%.

The missed detection rate should correspond to a specific monitorable data, comprising but not limited to $PM_1$, $PM_{2.5}$, $PM_{10}$, $PM_{100}$, sulfur dioxide, nitrogen oxides, ozone, carbon monoxide, VOCs (volatile organic compounds) or TVOC.

Therefore, the average undetected rate can be expressed as a set of indicators as follows:

m ($PM_1$, $PM_{2.5}$, $PM_{10}$, $PM_{100}$, sulfur dioxide, nitrogen oxides, ozone, carbon monoxide, VOCs, TVOC) or m ($PM_1$, $PM_{2.5}$, $PM_{10}$, $PM_{100}$, $SO_2$, $NO_X$, $O_3$, CO, VOCs, TVOC)

For example: m (N/A, 20%, 20%, N/A, N/A, N/A, N/A, N/A, N/A, N/A) means only consider monitoring data missed detection rate of $PM_{2.5}$, $PM_{10}$, the monitoring of other gaseous pollutants is temporarily not comprised in the system (N/A: Not Applicable).

Similarly, the release density also requires a set of indicators to reflect the release density of specific pollution monitoring equipment:

n ($PM_1$, $PM_{2.5}$, $PM_{10}$, $PM_{100}$, $SO_2$, $NO_X$, $O_3$, CO, VOCs, TVOC)

For m ($PM_{2.5}$)=20% and m ($PM_{10}$)=10%, it can be foreseen n($PM_{2.5}$)<n($PM_{10}$)

That is to say, the density of $PM_{10}$ monitoring equipment should be greater than the density of $PM_{2.5}$ monitoring equipment.

By adjusting the types and proportions of the sensor units of the multi-sensor monitoring equipment, a limited number of mobile monitoring vehicles with monitoring equipment installed can be fully utilized to achieve multiple air pollutant monitoring equipment to achieve the minimum delivery density index.

Therefore, the highest average undetected rate index $M_0$ and the corresponding lowest delivery density index $N_0$ are as follows:

$M_0$ ($PM_1$, $PM_{2.5}$, $PM_{10}$, $PM_{100}$, $SO_2$, $NO_X$, $O_3$, CO, VOCs, TVOC)

$N_0$ ($PM_1$, $PM_{2.5}$, $PM_{10}$, $PM_{100}$, $SO_2$, $NO_X$, $O_3$, CO, VOCs, TVOC)

Under a certain release density index, the rate of missed detection of this air pollutant can be effectively reduced by increasing the monitoring output frequency of the corresponding data of a certain area polluted by air pollutants.

Similarly, the hidden design of monitoring equipment can effectively prevent missed inspections caused by evasive behavior of polluting enterprises.

The method for determining the missed detection rate of urban air pollutant monitoring data proposed by the disclosure is as follows:

1) A monitoring system consisting of a fixed monitoring station, a monitoring center, and a mobile monitoring vehicle is first established in a monitoring area; the mobile monitoring vehicle is equipped with atmospheric pollutant monitoring equipment; and a set of the highest average leakage in the monitoring area is determined inspection rate index $M_0$;

2) Calculate a set of minimum delivery density index $N_0$ according to the set of highest average undetected rate index $M_0$;

3) Increase the number of mobile monitoring vehicles related to the delivery density index $N_0$, so that the set of the highest average undetected rate index $M_0$ is satisfied;

4) If there is a change in the set of the highest average undetected rate index $M_0$, perform step 2) and step 3) above again.

However, the first method has major flaws.

Considering the inconsistency of the correspondence between the distribution of the road network and the gridded area; mobile vehicles only operate in the range of the road network distribution, and there remains a very uneven coverage of the mobile vehicles: especially the mobile monitoring based on taxis, the probability of equipment appearing and staying on some sections is much greater than other remote or deserted sections.

In other words, when mobile devices are constantly moving, there is an uneven distribution of mobile devices in a large area.

If we measure according to whether there is enough monitoring data in each grid, we will find that there is redundant data in one part of the grid (mobile monitoring vehicles are piled up), and the other part is missing data (mobile monitoring vehicles appear rarely).

This phenomenon can be shown in FIG. 9, which counts the number of air pollution measurements by mobile monitoring equipment in each small grid, every 15 minutes is used as a timing unit. In a timing unit, multiple measurements of the same mobile device are calculated once.

The difference between a fixed point and a moving point is that the monitoring area of a single point is different. Fixed points can only cover a fixed-size area, and the coverage area changes because moving points change with time. Over a period of time (such as a day), it can cover a spatial range far beyond the fixed point. When the amount of data is met, the number of points covering the whole city of the mobile point is very different from the fixed points, so the estimation of the number of mobile points deployed throughout the city is a different problem from the fixed points, and the calculation theory of fixed points cannot be applied to solve.

At present, the data volume of the national control station for air pollution monitoring is based on one data per hour. Most of the air quality in cities is evaluated by daily average data, while mobile monitoring stations are mostly based on minute or second data. The mobile monitoring can achieve the effect of multiple fixed monitoring stations. When the vehicle-mounted mobile monitoring is performed in a continuous monitoring manner, it achieves a high coverage rate. When the mobile monitoring equipment is equipped with a taxi and other vehicles, it has more flexible and random locations. It is impossible to take measures in advance to affect air quality, and the data is more convincing.

Method 2: Measured by the distribution of the number of monitored units of each road section on the traffic network Considering the characteristics of mobile monitoring, we put our attention on the road network.

If the road network of an area (such as the urban area of a city) is divided into road segment units according to a certain granularity, that is, the length of road segment unit (such as every 100 meters, or 200 meters); we will carry the number of vehicles with mobile monitoring equipment (in working state) passing through each road section unit is an important indicator.

Further, in order to eliminate the short-term data repetition caused by multiple consecutive measurements, every 15 minutes or 30 minutes is used as a counting unit. In a counting unit, multiple passes of the same mobile device are counted only once. The data of different monitoring vehicles are accumulated.

If all road sections are spliced together, a long "band" is formed. According to the statistics for one day, we get the schematic of FIG. 10. The abscissa of the curve is each road segment unit; the ordinate is the cumulative monitoring times (detection count) of each road segment unit within a certain period of time (usually one day is selected).

Due to the differences between hot and cold sections, and the randomness of taxis, we can basically judge that in the statistical sense, the monitoring times on different sections of the unit is continuously superimposed according to time and shows the shape of a semi-normal distribution.

Here we need to define terms such as the monitoring times.

Road segment unit (RSU): length of which is defined to 100 meters, or 200 meters.

Monitoring times: In this article, specifically refers to the number of times that a certain road segment unit (RSU) has been monitored by a mobile monitoring vehicle; multiple passes of the same monitoring vehicle in a continuous counting period are counted only once.

The range of counting period 15 minutes, 30 minutes, or 1 hour.

Counting period: With a counting unit as the deadline, a new counting cycle is triggered when a monitoring vehicle enters a certain road segment unit (RSU); during the counting unit, the same monitoring vehicle entering the road section unit is no longer counted in the monitoring times. The counting cycle ends after one counting unit is present. The same monitoring vehicle can only have at most one counting cycle in each road section unit; a new counting cycle cannot be triggered before the end of the previous counting cycle.

FIG. 11 is a statistical distribution chart of the number of monitoring times (taxi) within a 24-hour period in a certain urban area by road segment unit.

It can be clearly seen from the figures that when there are only 50 taxis, only about 30% of the segment units in the 24 novels recorded more than 10 inspections.

With the gradual increase in the times of taxis equipped with monitoring equipment, more and more road units can record more than 10 inspections.

If we take 80% of the road section units can record more than 10 times in 24 hours as the expected indicators. Then as an example, it can be estimated that the times of taxis with monitoring equipment needs to reach 290.

Expected indicators: It is an index used to evaluate whether the amount of air pollution detection data collected within the road network of an urban area can reflect the overall pollution status. This indicator is characterized by two important parameters: covered range, and the number of scheduled detections.

Covered range: The number of scheduled detections of road section units that reach the predetermined monitoring times to the total number of road section units. The optional value range is between 50% and 90%. Generally, it is easy to select 70 to 80%.

False negative rate (Undetected Rate): which is opposite to Covered range. If covered range is 70%; then False negative rate is 100%−70%=30%.

Number of scheduled detections: When the monitoring times recorded by a road segment unit within a day reaches a certain value, the road segment unit is recognized as being covered by the test; otherwise, the road segment unit is considered an undetected segment. Generally speaking, considering the length of the counting unit, the selectable number of scheduled detections is 5-10 times.

Undetected segment: When the monitoring times recorded in a day does not reach the number of scheduled detections, the road segment unit (RSU) is considered to be undetected segment.

Under the model based on the monitoring times of road unit, for an air pollution detection object, we actually also set an average undetected rate index m when we set an expected indicator.

For situations where multiple pollutants need to be monitored, it is necessary to set individual expected indicators for each specific pollutant; considering different degrees of pollution hazards, different priorities for treatment, and different timings, each of the expected indicators may be significant difference. Taking FIG. 11 as an example, if the monitoring object is $PM_{2.5}$, its average undetected rate can be expressed as: m ($PM_{2.5}$, 80%, 10). Its meaning is: in an urban area, 80% of RSUs is able to record at least 10 tests (monitoring times) within 24 hours.

The disclosure discloses a method for determining the rated number of mobile monitoring vehicles. The method focuses on the traffic road network of an urban area, and it is implemented by installing air pollution detection equipment on mobile monitoring vehicles, especially taxis, to realize air quality monitoring of the urban area; the method comprises the following steps:

A) Establishing a curve model of monitoring times of mobile monitoring vehicles

1) For a certain urban area, decompose the road network into RSUs; establish and initialize a database of RSUs; this database contains the RSU number, RSU location, and RSU detection records (detection device number, accumulative time since each MMV enters each RSU, and the cumulative number of times of each the mobile monitoring vehicle (MMV) passes each RSU (which initial value is "0")).

2) Select a number of mobile monitoring vehicles (such as taxis) equipped with a positioning system, and track the number of times each mobile monitoring vehicle has passed each RSU (without detection equipment, it is equivalent to the number of virtual detections); in view of taxi drivers generally have a regional orientation. The number of taxis participating in the model construction should not be too small, there should be at least 50 vehicles generally.

3) Continue to record for at least one week; calculate the daily average of for each RSU;

4) Create the curve model of monitoring times for mobile monitoring vehicles, which is a statistical distribution of monitoring times for mobile monitoring vehicles by RSUs within 24 hours. In terms of cumulative time, the number of MMVs is modified to form a statistical distribution chart of the number of monitoring (taxi) by RSUs within 24 hours (as shown in FIG. 11); if the number of taxis participating in the model is 50, then the cumulative data for 2 days (daily average times 2) is equivalent to the curve of C=100; the cumulative data for 4 days is equivalent to the curve of C=200; and so on.

B) Determine the two parameters of the expected indicators (covered range, the number of scheduled detections)

C) According to the curve model of the number of detections, find out the curve that just meets the expected indicators, and get the requisite number or rated number ($C_0$) of the mobile monitoring vehicles.

When the number of taxis (mobile monitoring vehicles) exceeds the requisite number ($C_0$), the covered range of the RSU that can reach the number of scheduled detections will be further increased. However, the extent of this increase is limited, because some deserted road sections, remote road sections, or road sections designed for traffic control and other reasons have almost no possibility of being detected.

On the other hand, the emergence of certain air pollutants (such as car exhaust) is positively related to the active area of the taxi; this means that the places where taxis are less frequent are often has reduced the air pollution; therefore, when choosing a covered range, it is reasonable to give up properly tangling in some missed detection areas.

Method three, coexistence of two kinds of mobile monitoring vehicles (taxi, bus)

When buses are also involved in the monitoring of urban air pollution, the issue of coverage has changed significantly.

Buses usually have fixed routes, fixed covered range, fixed working hours, and fixed attendance. Therefore, buses are a special case of taxis when choosing a bus line with monitoring equipment, choosing a route with a low probability of taxi will play a supplementary information role. When reaching the same missed detection rate index, it helps to reduce the total number of mobile monitoring points.

When selecting a bus route with a low probability to install a mobile monitoring point, the amount of data monitored by one bus will have the effect of multiple taxis, and the calculation of the missed detection rate indicator is to meet the small probability route data amount to reach the minimum requirements, so the combination of the two will greatly reduce the total number of urban monitoring vehicles and save resources.

First, the bus usually runs back and forth along a fixed line; then the curve of the bus line is actually a smooth polyline corresponding to the model of the number of monitoring based on the section unit. As shown in the lower part of FIG. 12, the monitoring times of bus line B1 and B2 are evenly distributed on their respective running routes and on their respective section units.

If you compare line B1 and line B2, you will find that the bus line B1 contains a part of the road (the shaded part), which happens to fall in an area where taxis rarely appear.

Then, if the bus line B1 and the taxi cooperate to complete the monitoring of a certain pollutant, the bus line B1 can help cover the undetected segment that are difficult for the taxi to cover.

In other words, the combination of bus line B1 and taxi can significantly increase the covered range of pollution detection as a whole.

And the bus line B2, because its path is all located in the covered range of the taxi, installing detection equipment on B2 cannot significantly increase the covered range of pollution detection as a whole.

When there are multiple alternative bus lines, how to determine which bus lines are equipped with detection equipment is a very meaningful technical issue.

The disclosure discloses a method for selecting a bus line to participate in monitoring during the coordinated monitoring of taxis and buses:

A) Establish a taxi detection frequency curve model

1) For a certain urban area, decompose the traffic road network in units of road units; establish and initialize a database of each road unit; this database contains the road unit number, road unit location information, and road unit detection records (detection device number, time when entered the road section unit, and the cumulative number of times passed the road section unit (initial value is "0"))

2) Select a part of the mobile monitoring taxi equipped with a positioning system, and track the number of times each mobile monitoring taxi has passed in different sections of the road (without detection equipment, it is equivalent to the number of virtual detections); in view of taxi drivers generally have a regional orientation. The number of taxis participating in the model construction should not be too small, there should be at least 50 vehicles generally.

3) Continue to record for at least one week; calculate the daily average after accumulating daily statistical data;

4) In terms of cumulative time, the number of mobile monitoring cars is changed to form a statistical distribution chart of the number of monitoring (taxi) by road unit within 24 hours (as shown in FIG. 11); if the number of taxis participating in the model is 50, then the cumulative data for 2 days (daily average times 2) is equivalent to the curve of C=100; the cumulative data for 4 days is equivalent to the curve of C=200; and so on. (2) Establishing a curve model of the number of detections for each bus line.

B) Establishing a curve model of the monitoring times for each bus line

Its horizontal axis is consistent with the horizontal axis of the taxi detection frequency curve model; according to the operation plan of the bus line, the monitoring times is assigned to the corresponding road section unit.

C) Sort each bus line according to the number of undetected segments the each bus line covers 1) First select an initial value of the covered range $f_0$ (such as 70% or 80%); the initial value of the loop variable i=0;
2) i=i+1;
3) determine the bus line that has the most undetected segments and rank i;
4) Calculate the local coverage area $b_i$ (percentage %) corresponding to the undetected segments covered by the bus line ranked i;
5) Subtract the covered range $b_i$ from the covered range $f_{(i-1)}$ to obtain the new covered range $f_i$ and the new undetected segment; the new undetected segment should deduct the leakage that has been covered by the bus line in front;
6) From the remaining bus lines, continue to select the bus line that has the most undetected segment, and rank i+1;
7) Repeat steps 2) to 6) until the sorting is completed;

D) Select the bus routes participating in collaborative monitoring according to the order of step 3).

Adjustment of the Number of Taxis

As the optimized bus lines can partially cover the road units that are difficult for taxis to effectively cover, the number of taxis can be appropriately reduced while maintaining the overall covered range unchanged.

As shown in FIG. 12, since the bus line B1 can cover the road unit represented by $b_1$, the rated number of taxis can be reduced from the original 290 to 140.

E) Determining two parameters of the expected indicators (covered range f, the number of scheduled detections);

F) For each selected bus line $B_i$ its local covered range $b_i$ is sequentially subtracted from the covered range f to obtain a new covered range $f^{1-}$;

J) With the new covered range f' and the number of scheduled detections, the curve model of the monitoring times of taxi is used to find the curve that just meets the expected indicators, and the rated number of taxi cars ($C_0$) is obtained.

High/Low Frequency Sensors

The earlier application PCT/IB2018/05531 discloses an air pollution detection device, which comprises a control module and a detection module; the detection module uses at least four sub-sensor units to form a sensor module; when the control module finds an abnormal suspected sub-sensor occurs and it is determined to be an abnormal sub-sensor, the abnormal sub-sensor is classified into an isolation area, and the multi-core sensor module continues to be normal after degrading jobs.

This application further discloses another type of air pollution detection device. The air pollution detection device comprises a control module and a detection module; the detection module comprises at least two similar sub-sensor units to form a sensor module; and the sub-sensor units work at normal operating frequency. The detection module further comprises at least one sub-sensor unit similar to the sensor module to form a low-frequency calibration module; the sub-sensor unit in the low-frequency calibration module operates at a frequency much lower than the operating frequency of the sensor module. Therefore, the low-frequency calibration module is also called a low-frequency group. For comparison, the sensor module is also called a high-frequency group.

Generally, the operating frequency of the sensor module is 10 times or more than that of the low-frequency calibration module. The ratio of the working frequency of the high frequency group to the low frequency group is called the high frequency and low frequency ratio, and can be selected as: 2:1, 3:1, 4:1, 5:1, 6:1, 7:1, 8:1, 9:1, 10:1, 15:1, 20:1.

The working frequency of the low frequency group can be consistent with the rhythm of abnormal judgment. That is, when it is necessary to determine whether there is the phenomenon of an abnormal sub-sensor in the sensor module, the low-frequency group performs the detection work.

Because the laser power attenuation is slow in most of the working life of the laser sensor, the accuracy of its data can be restored by calibration; that is, the sub-sensor that is not attenuated or has a very low attenuation is used to calibrate the high-attenuated sub-sensor.

During the operation of the sensor module, every certain time, such as 1 day, 1 week, or 1 month, use the low-frequency group detection data as a reference to calibrate the high-frequency group detection data, and the calibration coefficient can be obtained by the ratio of the average value of the detection data of the high-frequency sensor set to the average value of the detection data of the low-frequency sensor set.

In addition to the light attenuation effect of laser sensors, other types of sensors may also have a tendency of unstable performance or increased data errors under long-term high-load working conditions. By introducing a low-frequency group, it can be used as a relatively reliable reference to determine whether there is a data shift phenomenon in the sensor module.

At the same time, since the data of the low-frequency group is generally more reliable, when determining which sub-sensor unit in the sensor module is suspected to be abnormal or abnormal, a more reliable judgment can be made by increasing the data weight of the low-frequency group. A simple solution is that all the low-frequency groups of data are involved in the judgment of suspected anomalies with twice the weight.

Isolation and Recovery

The earlier application PCT/IB2018/05531 also discloses a method for identifying the working state of the sub-sensor and isolation and recovery the sub-sensor. The sensor module obtains a set of detection data at a time, and the control module filters out suspected abnormal data from this set of data, and then determines whether the corresponding sub-sensor meets the isolation condition. The sub-sensor was judged to be abnormal sub-sensor and then classified into the isolation zone; after judging that the suspected abnormal sub-sensor does not meet the isolation condition, the sub-sensor continues to work normally. Determine whether the sub-sensor entering the isolation area can self-heal. If it can self-heal, the frequency reduction will be performed. However, the output data of the sub-sensor will not participate in the calculation of the output data of the main control module. For sub-sensors that cannot self-heal, stop working and notify the operator to repair or replace them. For the sub-sensor after frequency reduction, the control module detects its output data to judge whether it meets the recovery condition. The sub-sensor that meets the recovery condition is removed from the isolation zone and resumed work. The output data is involved in the calculation of sensor module data or master control data. For the abnormal sub-sensor that does not meet the recovery condition, whether it can be self-healing is determined again.

After isolating the abnormal sub-sensors in the sensor module, the average value of the remaining sub-sensor output data is used as the output result of the sensor module, and the sensor module can continue to be used normally.

Further, the combination of the sensor units in the detection module is selected according to the distribution characteristics of the air pollutants contacted by the mobile monitoring vehicle, so that the selection of the detection module matches the distribution characteristics of the air pollutants contacted by the mobile monitoring vehicle.

In addition, by optimizing the combination of the sensor units in the detection module, the number of the mobile monitoring vehicles that need to be placed can be minimized when a set of the highest average undetected rate index $M_0$ is satisfied.

Traditional monitoring methods, such as special monitoring vehicle detection and personnel on-site inspection methods, monitor personnel can control the time and place of monitoring, so that monitoring is not random and sudden. It is also possible for polluting companies to know the time and place of detection from the operators of these devices in various ways, so that polluting companies can avoid monitoring and have room to operate. This scheme uses social vehicles such as taxis as mobile monitoring vehicles to monitor atmospheric pollutants. The driving paths and time of social vehicles are not for monitoring purposes, and the monitoring locations and times are not subject to human control. At the same time, the monitoring equipment is not controlled by the driver. This way of monitoring is more random and flexible. The big data processing can ensure the objectivity of the atmospheric pollutant monitoring data after a reasonable amount of monitoring equipment is put in.

At the same time, the monitoring of atmospheric environmental pollution needs to be hidden. When traditional monitoring methods such as special monitoring vehicles and personnel conduct on-site monitoring, polluting enterprises can also timely detect and adjust the production of pollution; for fixed monitoring sites, polluting enterprises can also be targeted take corresponding countermeasures, such as changing the way of sewage outlet. In this solution, the monitoring equipment is concealed inside or under the taxi roof lights, bus roofs, etc., so that the polluting enterprises and individuals being monitored cannot know that nearby equipment is monitoring atmospheric pollutants around them, making the monitoring data objectivity has further improved. As shown in FIG. 5, the sewage company will not know that the taxi passing by the door is monitoring its pollutants.

At the same time, the system is designed in a variety of ways to prevent data tampering, making monitoring more objective.

There are other characteristics of using social vehicles: the characteristics of buses are that the routes are relatively fixed, which is conducive to repeated measurements on a certain road section, and it can give more reliable and more time data. There are more buses that send shifts and the interval time is compared even. When there are many shifts, it is usually the rush hour, and it is also the period when the particulate matter is polluted. The characteristics of taxis are that they have a wide distribution range and a wide time range. They can measure the places that buses cannot reach, and the measurement time range supplements the periods when buses are not in operation. The driving route of the muck truck is often the road dust pollution section. Let such measurements focus on monitoring the dust road section, which can do more with less effort, and can also measure the dust pollution situation of your own vehicle. The comprehensive data of multiple dump trucks is road dust background data. The data of the own vehicle comprises the background and the pollution of the own vehicle. Through the big data processing, the two types of data can be separated, and the road and self-pollution can be evaluated separately, facilitate control.

The feature of long-distance buses is that they can cover the blind spots of monitoring between cities and form a larger range of monitoring.

Using social vehicles such as taxis to monitor atmospheric pollutants can more easily find areas with higher environmental health risks, because people-populated areas are hotspots and areas where these social vehicles appear more frequently. Repeated monitoring of these areas can obtain more accurate pollution information in densely populated areas, enabling environmental management departments to deal with pollution problems in a more targeted manner. At the same time, the height of the taxi ceiling light is basically the same as the height of the mouth and nose of the personnel at which the personnel mainly breathe. Using a taxi equipped with atmospheric pollutant monitoring equipment to monitor the atmosphere at this height can effectively reflect the impact on people's breathing. It is of great significance for the governance of the atmospheric environment.

Environmental monitoring, especially grid-based monitoring, is relatively expensive. The disclosure is also beneficial in that the device uses social vehicles such as city buses, long-distance buses, taxis, dirt trucks, etc. to carry out real-time measurement with air pollutant sensors dedicated venues and professional operators are not required, and low one-time investment requirements reduce the cost of measurement. At the same time, it reduces the energy consumption and road occupation brought by special vehicles. In the end, the occupation of public resources and the cost of air pollutant monitoring are decreased.

The air pollutant monitoring equipment comprises a detection module, a control module and a communication module; the detection module contains one or more air pollutant sensor units; the air pollutant sensor unit is one of the following sensors: $PM_1$, sensor, $PM_{2.5}$ sensor, $PM_{10}$ Sensor, $PM_{100}$ sensor, $NO_X$ sensor, $O_3$ sensor, $SO_2$ sensor, VOCs sensor or TVOC sensor.

The control module is connected to the power source of the mobile monitoring vehicle. It supplies power to the detection module and the communication module on the atmospheric pollutant monitoring equipment. The control module is connected to the detection module and the communication module on the atmospheric pollutant monitoring equipment through a data interface, and performs data exchange with the detection module communication module.

Figure 1:
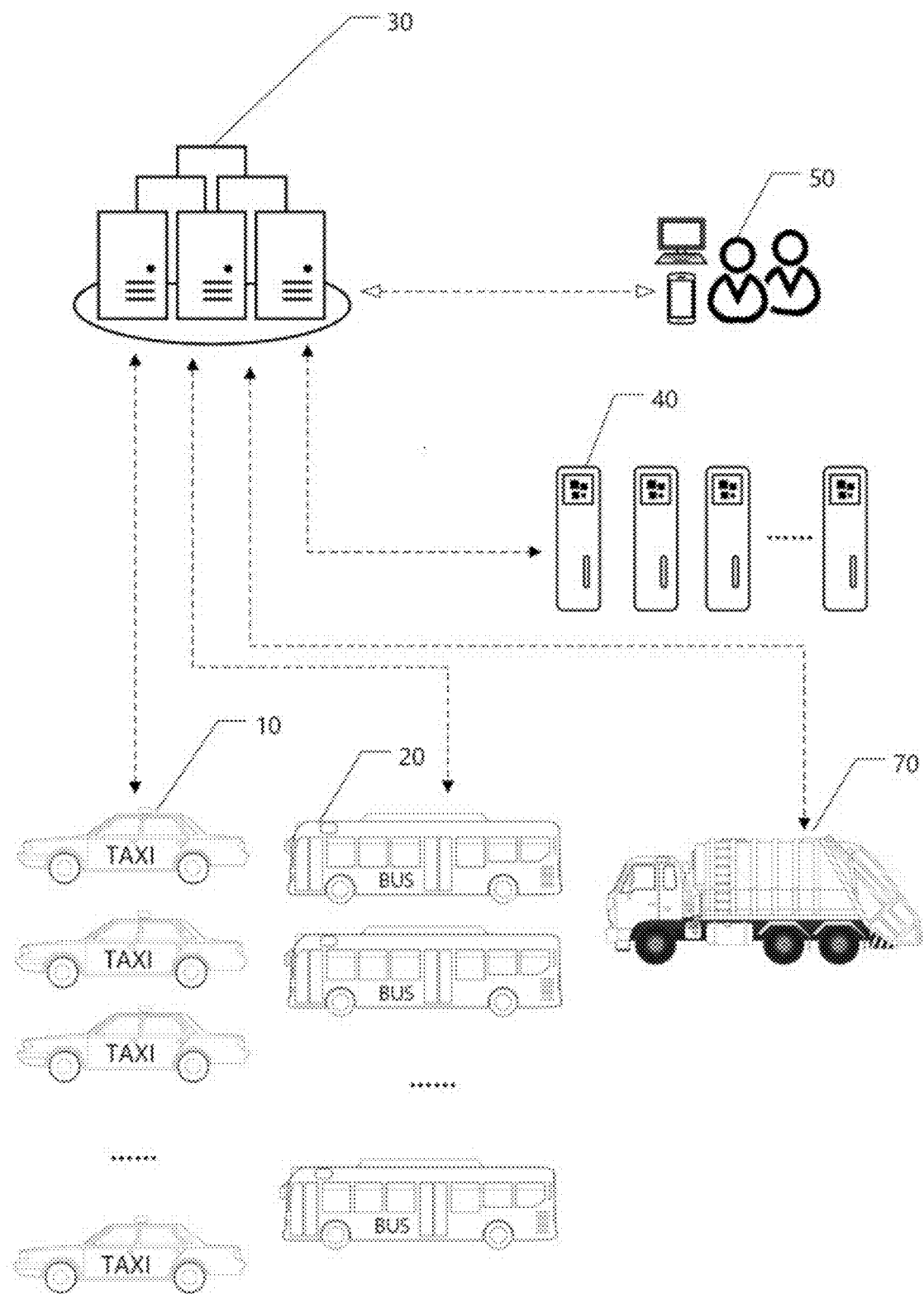
FIG. 1 is a schematic diagram of a system composition of the disclosure.
Figure 2:
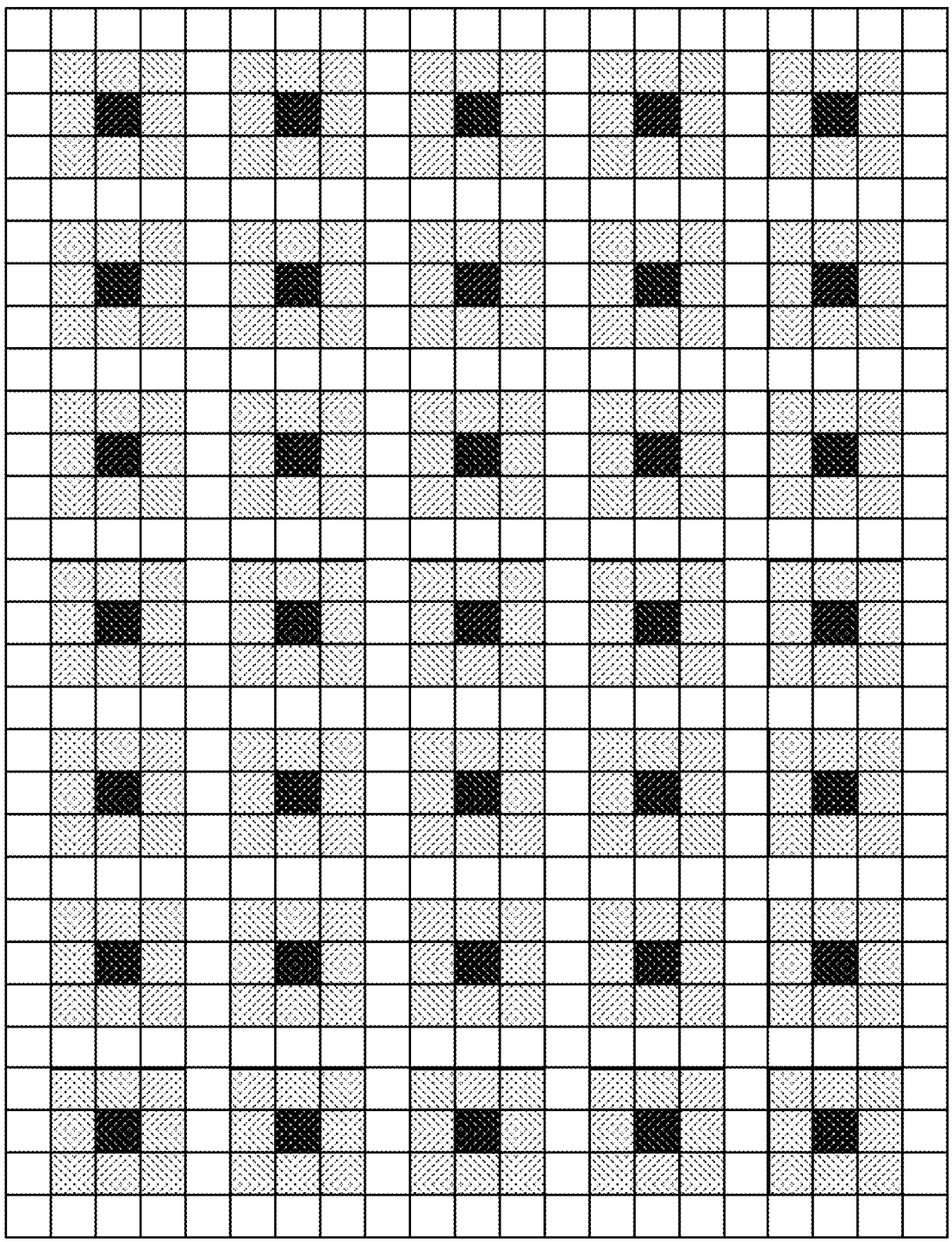
FIG. 2 is a schematic diagram of a grid-based fixed monitoring site layout mode.

In the drawings, 10—taxi, 20—bus, 30—monitoring center, 40—fixed monitoring station, 50—user terminal, 70—other social vehicles, 60—air pollution monitoring equipment, 601—detection module, 602—video acquisition module, 603—communication module, 604—control module;

In the drawings, C—the number of taxi (monitoring car), $C_0$—the rated number of taxi (monitoring car), $b_1$—the local covered range (percentage) corresponding to the undetected segment of the bus line $B_1$; $f_0$—covered range initial value; $f_1$—new covered range (considering $b_1$).

DETAILED DESCRIPTION

Example 1

A method and system for improving the accuracy of air pollutant monitoring data, using social vehicles to carry air pollutant monitoring equipment, comprising air pollutant monitoring equipment, a monitoring center, a fixed monitoring site, and a user terminal, as shown in FIG. 1.

Air pollutant monitoring equipment is installed on social vehicles to monitor the quality of the atmospheric environment where the vehicle is located. The air pollutant monitoring equipment has an information transmission function and can return the monitored data, location data and time information wirelessly to the monitoring center. It also can record road conditions and record road pollution, and can transmit the collected video back to the monitoring center. The air pollutant monitoring equipment has the function of storing data and video data, and saves the collected data and video data locally. The air pollutant monitoring equipment further comprises a data transmission interface, which can copy the saved data and video data to local maintenance or staff through local transmission.

The monitoring center can not only receive data returned from atmospheric pollutant monitoring equipment and store and process these data, but also collect data from other types of monitoring equipment, such as collecting data from miniature fixed monitoring sites, and collecting data from nearby fixed monitoring sites. The monitoring center can combine the data from the air pollutant monitoring equipment of social vehicles, the collected data from the miniature fixed monitoring stations, and the collected data from nearby fixed monitoring stations to generate a data list and data ranking and pollution clouds, historical playback and other data presentation methods. These processing result files are sent to user terminals through the network, and users can query and use them according to their needs. The monitoring center can also remotely control the operation of atmospheric pollutant monitoring equipment, such as turning on and off atmospheric pollutant monitoring equipment, turning on and off video acquisition modules, adjusting monitoring frequency, and correcting errors in atmospheric pollutant monitoring.

Example 2

The objective air pollutant monitoring data of a city can only reflect the true degree of air pollution in the city. The disclosure needs to set a series of the highest average undetected rate index $M_0$ to represent the objectivity of the monitoring data. For example, a city needs to monitor $PM_{10}$, and its undetected rate is expressed as m ($PM_{10}$). If the city requires m ($PM_{10}$)<20%, it means that the $PM_{10}$ pollution event not captured by the monitoring equipment is less than 20% of the total $PM_{10}$ pollution event.

In order to achieve m ($PM_{10}$)<20%, the minimum delivery density index $N_0$ is introduced. $N_0$ represents the minimum delivery density index of the monitoring equipment required to reach $M_0$. In this example, in order to reach m ($PM_{10}$), the minimum delivery density of the monitoring equipment equipped with a $PM_{10}$ sensor is n ($PM_{10}$). The n ($PM_{10}$) needs to be calculated based on the area of the city, the number of vehicles equipped with mobile monitoring equipment, the daily mileage of vehicles, the driving range of vehicles, the type of vehicles, and the accuracy of equipment installed, etc. The area of the city is directly proportional to the amount of monitoring equipment that needs to be deployed; the daily mileage of the vehicle and the vehicle exercise are inversely proportional to the amount of monitoring equipment that needs to be deployed.

Example 3

$PM_{10}$ and $SO_2$ of a city are monitored. In the disclosure, the highest average undetected rate index $M_0$ of this city is expressed as m ($PM_{10}$), m ($SO_2$). Different pollutants have different levels of pollution contribution, and cities attach different degrees of importance, so the average undetected rate for different pollutants will have corresponding requirements. Generally, cities attach less importance to the monitoring of $SO_2$ than $PM_{10}$. In this example, the highest average undetected rate of $PM_{10}$ and $SO_2$ is set to m ($PM_{10}$)=20% and m ($SO_2$)=30%.

When m ($PM_{10}$)=20%, m ($SO_2$)=30%, only taxis are equipped with monitoring equipment that can only monitor $PM_{10}$ or $SO_2$, the minimum delivery density n ($PM_{10}$) of the monitoring equipment will be greater than n ($SO_2$), that is, more taxis equipped with $PM_{10}$ monitoring equipment than taxis equipped with $SO_2$ monitoring equipment.

Example 4

$PM_{10}$ and $SO_2$ of a city are monitored. In the disclosure, the highest average undetected rate index $M_0$ of this city is expressed as m ($PM_{10}$), m ($SO_2$). In this example, the highest average undetected rate of $PM_{10}$ and $SO_2$ is set to m ($PM_{10}$)=20% and m ($SO_2$)=30%. Current monitoring equipment can also measure multiple pollutants simultaneously through the combination of internal detection modules.

The first launch method in this example is that all vehicles are equipped with monitoring equipment that can simultaneously measure $PM_{10}$ and $SO_2$. Then the $N_0$ minimum monitoring equipment release density index only needs to meet the strictest highest average undetected rate in the index. The first method is n ($PM_{10}$)=n ($SO_2$), and the specific n ($PM_{10}$) value is calculated the parameter relationship of the city area and the delivery density index described in Example 2.

The second method of launch in this example is that some vehicles are equipped with monitoring equipment that can both measure $PM_{10}$ and $SO_2$, and other vehicles are equipped with vehicles that can only measure $PM_{10}$ equipment. At this time, n ($PM_{10}$)>n ($SO_2$), specific n ($PM_{10}$) and n ($SO_2$) need to be calculated and finally satisfy m ($PM_{10}$)= 20%, m ($SO_2$)=30%.

Example 5

Dust pollution in cities is mainly reflected in the value of $PM_{10}$, and muck trucks are a major contribution to dust pollution. If the city needs to monitor $PM_{2.5}$ and $PM_{100}$, the highest average undetected rate indicator is m ($PM_{10}$)=m ($PM_{100}$)=20%. The distribution density can be distinguished according to the vehicle. By mounting $PM_{100}$ monitoring equipment on the slag truck, it can more effectively monitor the dust pollution and more effectively achieve the density index of $PM_{100}$ monitoring equipment. $PM_{2.5}$ monitoring equipment has more assigned to small vehicles such as taxis.

Example 6

The basic modules of air pollutant monitoring equipment comprise a detection module, a main control module and a communication module. The control module is connected to the power source of the mobile monitoring vehicle, and provides power for the detection module and the communication module. The control module is connected to the detection module and the communication module on the air pollutant monitoring equipment through a data interface, and performs data exchange with the detection module and the communication module. For example, the data collected by the detection module is processed by the control module and sent to the communication module, which is then returned to the monitoring center; the instructions sent by the monitoring center are received by the communication module and transmitted to the control module. The control module adjusts the detection according to the instructions Module operation. The control module has the function of storing and exporting data and video data. The control module has a positioning function or a data interface with a positioning device, and uses GPS, Beidou and other positioning technologies to record the vehicle position in real time.

Example 7

The basic modules of air pollutant monitoring equipment comprise a detection module, a control module and a communication module. The detection module detects the pollutant content of the sampled gas through the air pollutant sensor mounted on it, and obtains the concentration data of the pollutant. The detection module can be equipped with a variety of air pollutant sensors, comprising $PM_1$ sensor, $PM_{2.5}$ sensor, $PM_{10}$ sensor, $PM_{100}$ sensor, nitrogen oxide sensor, ozone sensor, sulfur dioxide sensor, VOCs sensor or TVOC sensor for pollutant monitoring. For example, air pollutant monitoring equipment equipped with $PM_{2.5}$ sensors and $PM_{10}$ sensors can better monitor road dust, and can timely detect road dust pollution and provide early warning.

The detection module can also be equipped with other types of sensors, such as wind speed sensor, wind direction sensor, temperature sensor, humidity sensor, pressure sensor, and noise sensor, to provide richer monitoring information. And for example, the humidity sensor can provide humidity correction and calibration basis for the atmospheric pollutant sensor.

Example 8

The basic modules of air pollutant monitoring equipment comprise a detection module, a control module and a communication module. The communication module is used for wireless communication between the atmospheric pollutant monitoring equipment and the monitoring center, uploading monitoring data, location information, time information and monitoring video, and can also receive instructions issued by the monitoring center to adjust the operation of the atmospheric pollutant monitoring equipment. The communication module communicates with the monitoring center using data transmission methods such as GPRS, 4G, 5G, Bluetooth, WIFI, LoRaWAN, and narrowband Internet of Things. It returns data to the monitoring center in real time, and the interval of each data return is in seconds.

Example 9

In addition to basic modules, air pollutant monitoring equipment can also be equipped with video acquisition modules that is used to collect evidence of pollutants, to visualize the degree of pollution, to facilitate later law enforcement, and to determine the source of pollution. The video acquisition module is equipped with a camera, which can upload the road conditions captured to the monitoring center.

Example 10

Mobile monitoring vehicles equipped with atmospheric pollutant monitoring equipment are social vehicles. Social vehicles comprise city buses, long-distance buses, taxis, earthmoving vehicles, municipal vehicles, official vehicles, ride-hailing vehicles, rental vehicles, shared vehicles, and vehicles with autonomous driving functions. These social vehicles do not need a dedicated site, and professional operators can perform real-time measurement of air pollution. The one-time investment is low, which reduces the energy consumption and road occupation brought by special vehicles. In the end, the occupation of public resources and the cost of air pollutant monitoring are decreased.

Example 11

Install air pollution monitoring equipment equipped with particulate matter sensors on the bus. The characteristic of the bus is that the route is relatively fixed. Using one or several buses equipped with atmospheric particulate sensor monitoring equipment can monitor atmospheric particulate pollution along the entire bus line, reducing the monitoring cost. At the same time, due to the characteristics of the bus, it is possible to repeatedly measure a certain road section multiple times, which can give more reliable and more time data. The interval between buses is relatively even and there are many vehicles. When there are many shifts, it is usually the peak traffic time, and it is also the period when the particulate matter is polluted.

Example 12

Atmospheric pollutant monitoring equipment equipped with particulate matter sensors is installed on large social vehicles such as dirt trucks, garbage disposal trucks, and long-distance vehicles. These large social vehicles often run on roads with severe dusting. Using these large social vehicles to monitor key dusting sections will do more with less. At the same time, you can also measure the dust pollution of your own vehicles. The data detected by these large social vehicles comprise the background pollution and the pollution of their own vehicles. Through the big data processing, the two types of data can be separated, and the road and self-pollution can be evaluated separately to facilitate control.

The feature of long-distance buses is that they can cover the blind spots of monitoring between cities and achieve a wider range of monitoring.

Example 13

Install air pollution monitoring equipment equipped with particulate matter sensors on taxis. Taxi is characterized by a wide distribution range and a wide time range, which can measure places that other social vehicles cannot reach. Using social vehicles such as taxis to monitor atmospheric pollutants can more easily find areas with higher environmental health risks, because people-populated areas are hotspots and areas where these social vehicles appear more frequently. Repeated monitoring of these areas can obtain more accurate pollution information in densely populated areas, enabling environmental management departments to deal with pollution problems in a more targeted manner. At the same time, the height of the taxi ceiling light is basically the same as the height of the mouth and nose of the personnel at which the personnel mainly breathe. Using a taxi equipped with atmospheric pollutant monitoring equipment to monitor the atmosphere at this height can effectively reflect the impact on people's breathing. It is of great significance for the governance of the atmospheric environment.

Figure 3:
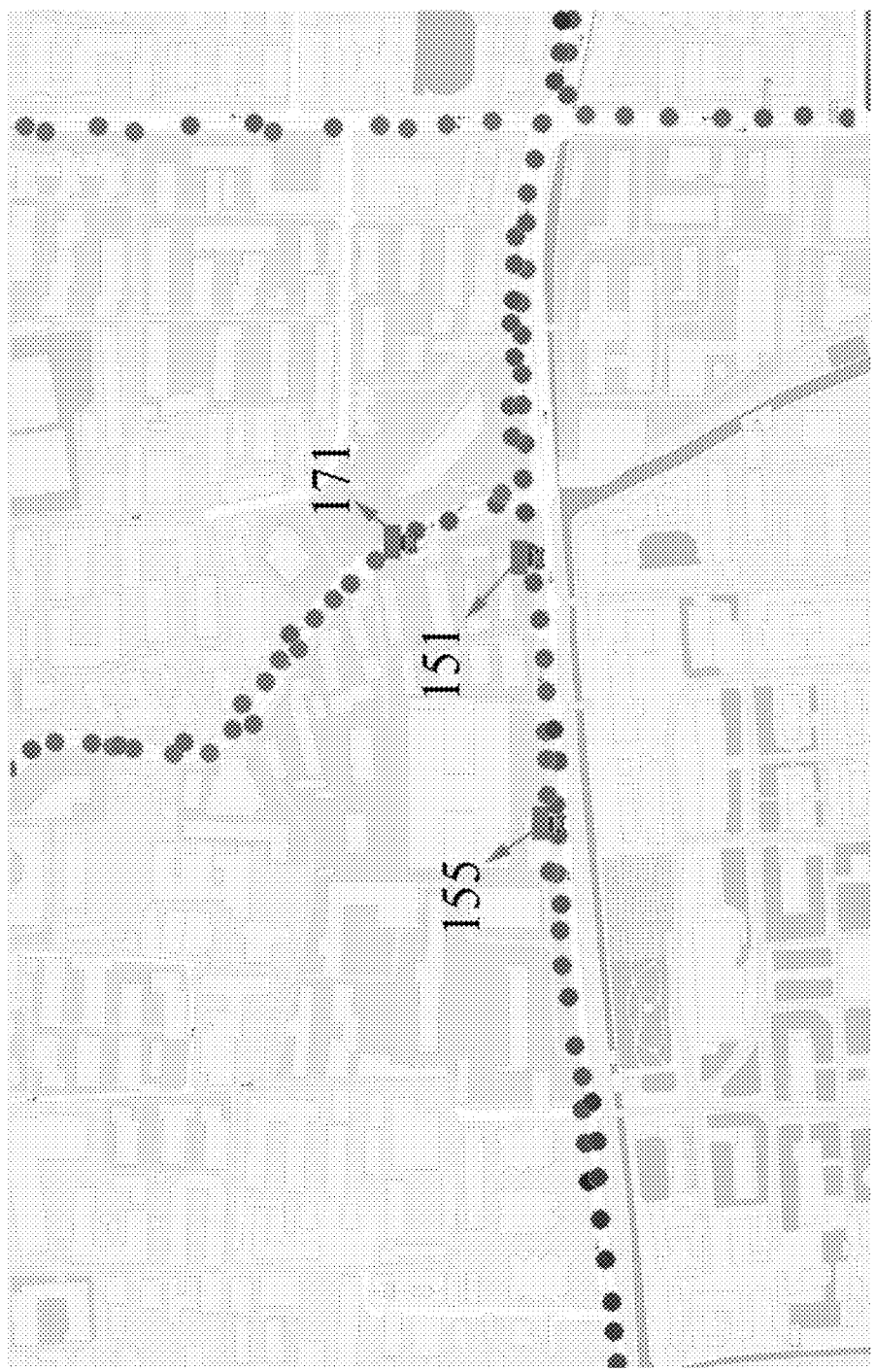
FIG. 3 is a schematic diagram of an example monitoring platform in a city in Shandong.
Figure 4:
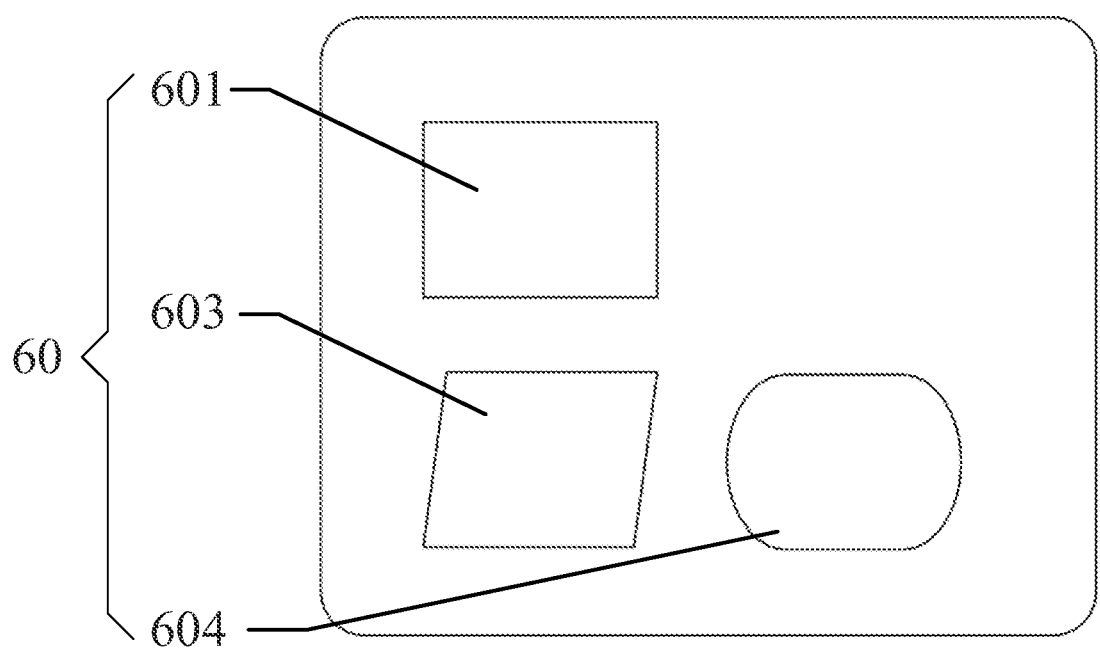
FIG. 4 is a schematic diagram of a basic module composition of an air pollutant monitoring equipment.

FIG. 3 shows the monitoring results of a taxi equipped with atmospheric particulate monitoring equipment in a city in Shandong. A total of about 100 vehicles that a total trip of more than 23,000 kilometers per day can generate 1.2 million sets of data. Through the big data processing platform of the monitoring center, these data can automatically generate urban haze maps. Technicians can further judge whether the supervision of pollution sources in the relevant area is in place, and guide the precise treatment plan. The monitoring center also ranks districts, counties, sub-district offices and road sections to provide technical means for governance assessment.

Example 14

Figure 5:
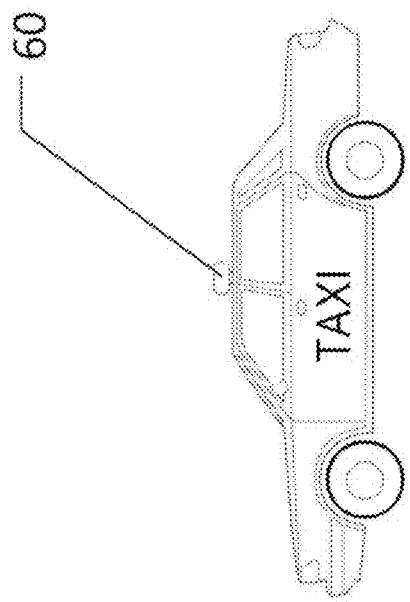
FIG. 5 illustrates the concealment using social vehicle monitoring.
Figure 5:
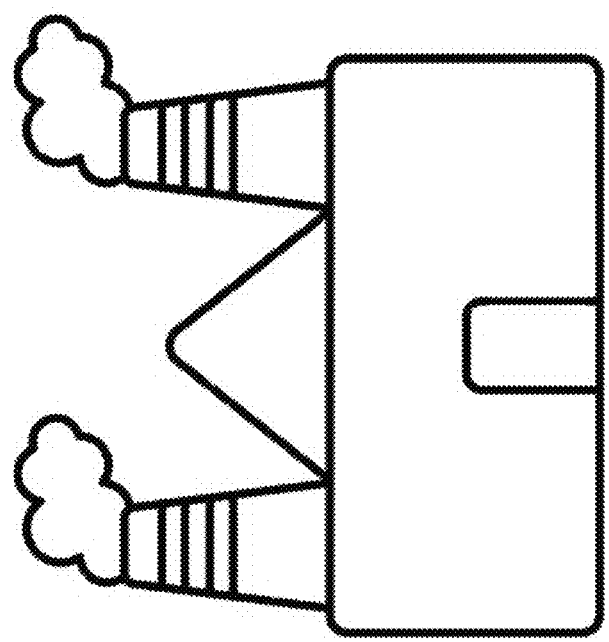
Figure 6:
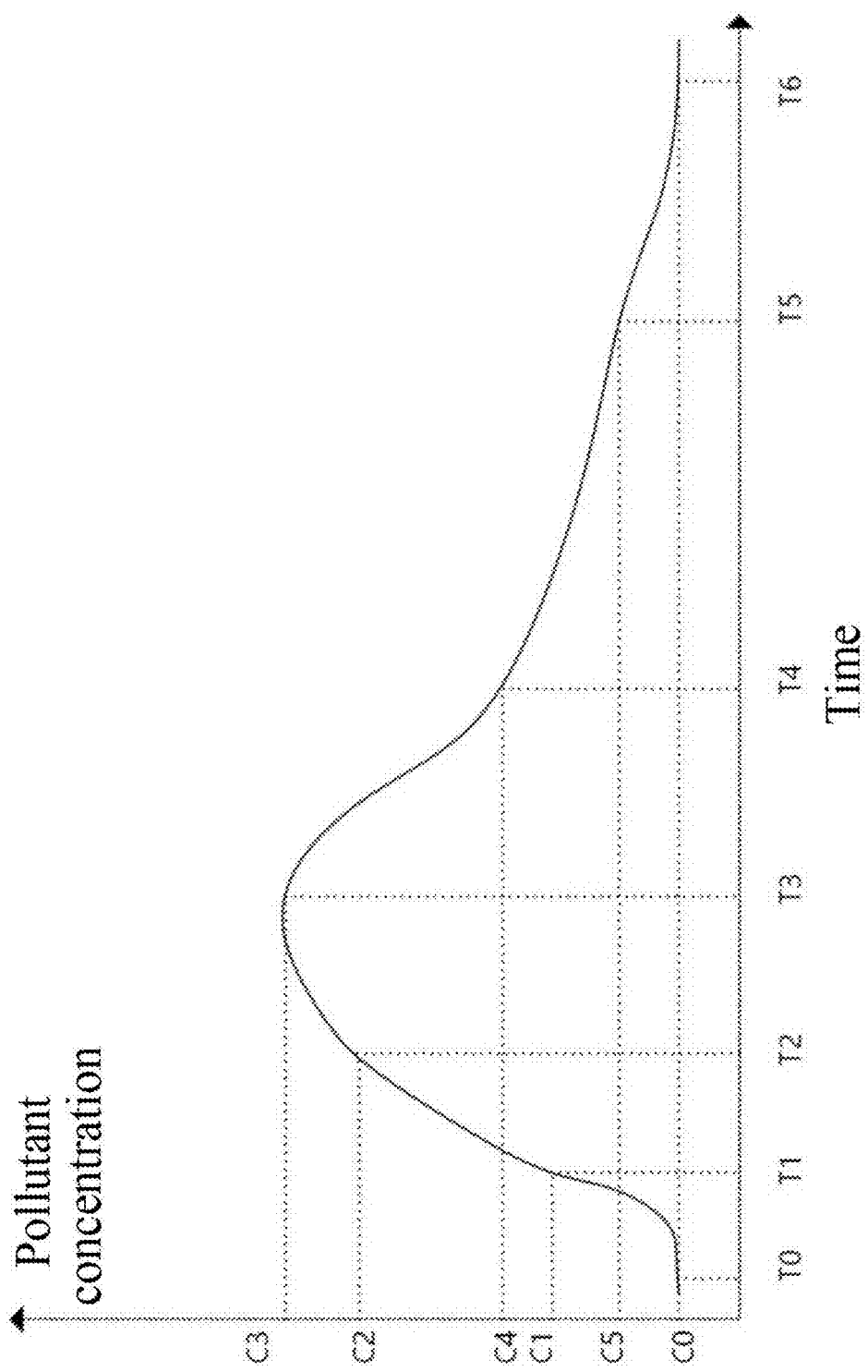
FIG. 6 shows the characteristics of air pollution, which is time-sensitive.
Figure 7:
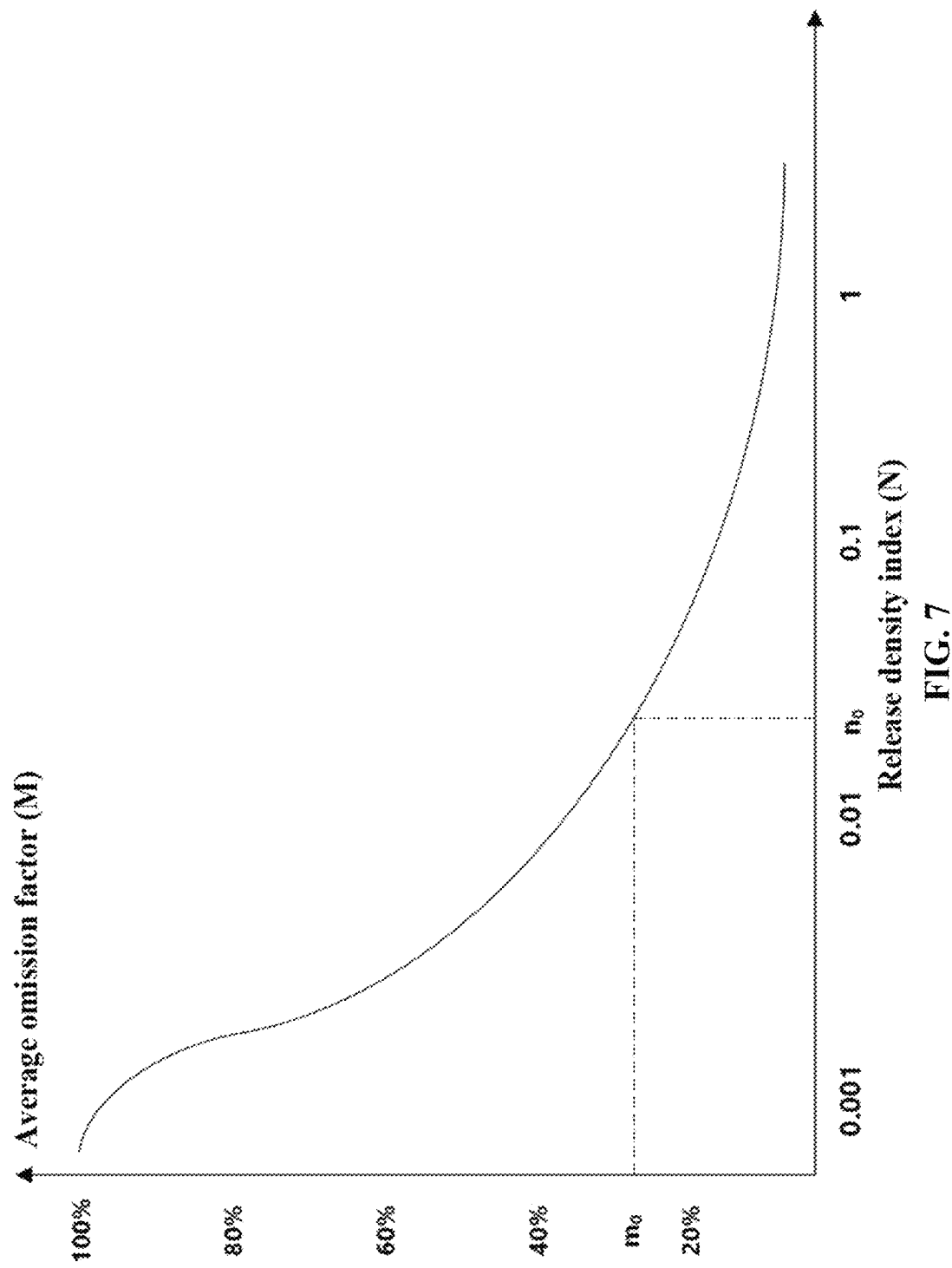
FIG. 7 shows the relationship between the average undetected rate and the monitoring equipment release density index.
Figure 8:
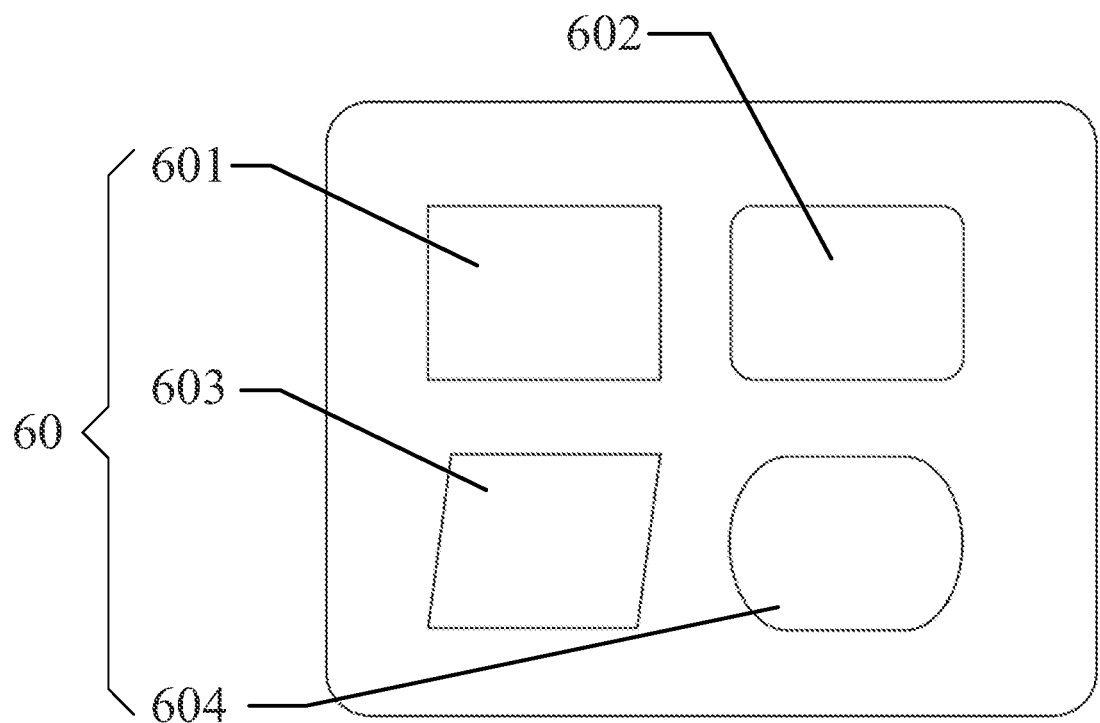
FIG. 8 is a schematic diagram of an air pollutant monitoring equipment comprising a video acquisition module.
Figure 9:
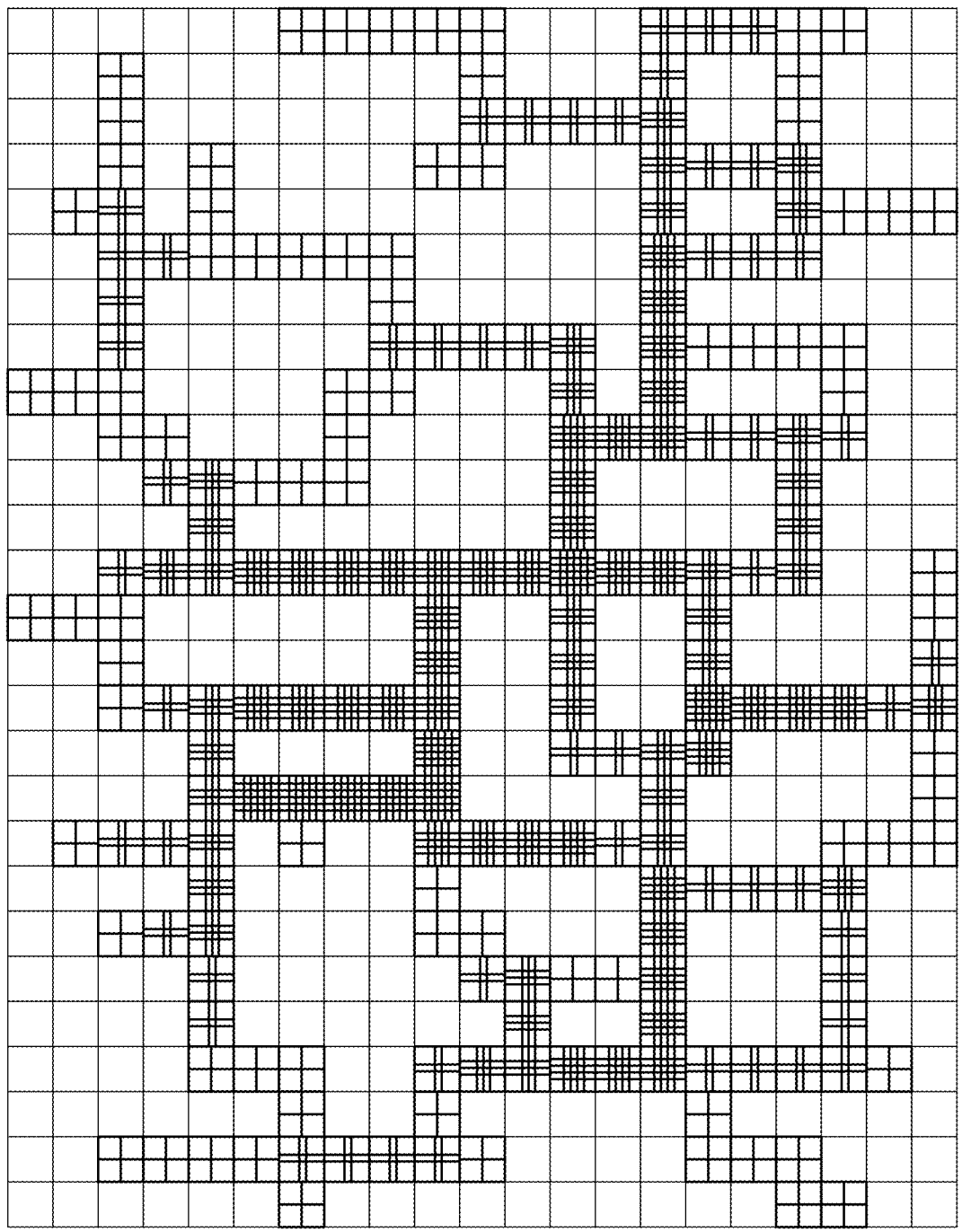
FIG. 9 is a schematic diagram of a distribution of detection data in a grid in a mobile monitoring mode.
Figure 9:
Figure 9:
Figure 9:
Figure 9:
Figure 9:
Figure 9:
Figure 10:
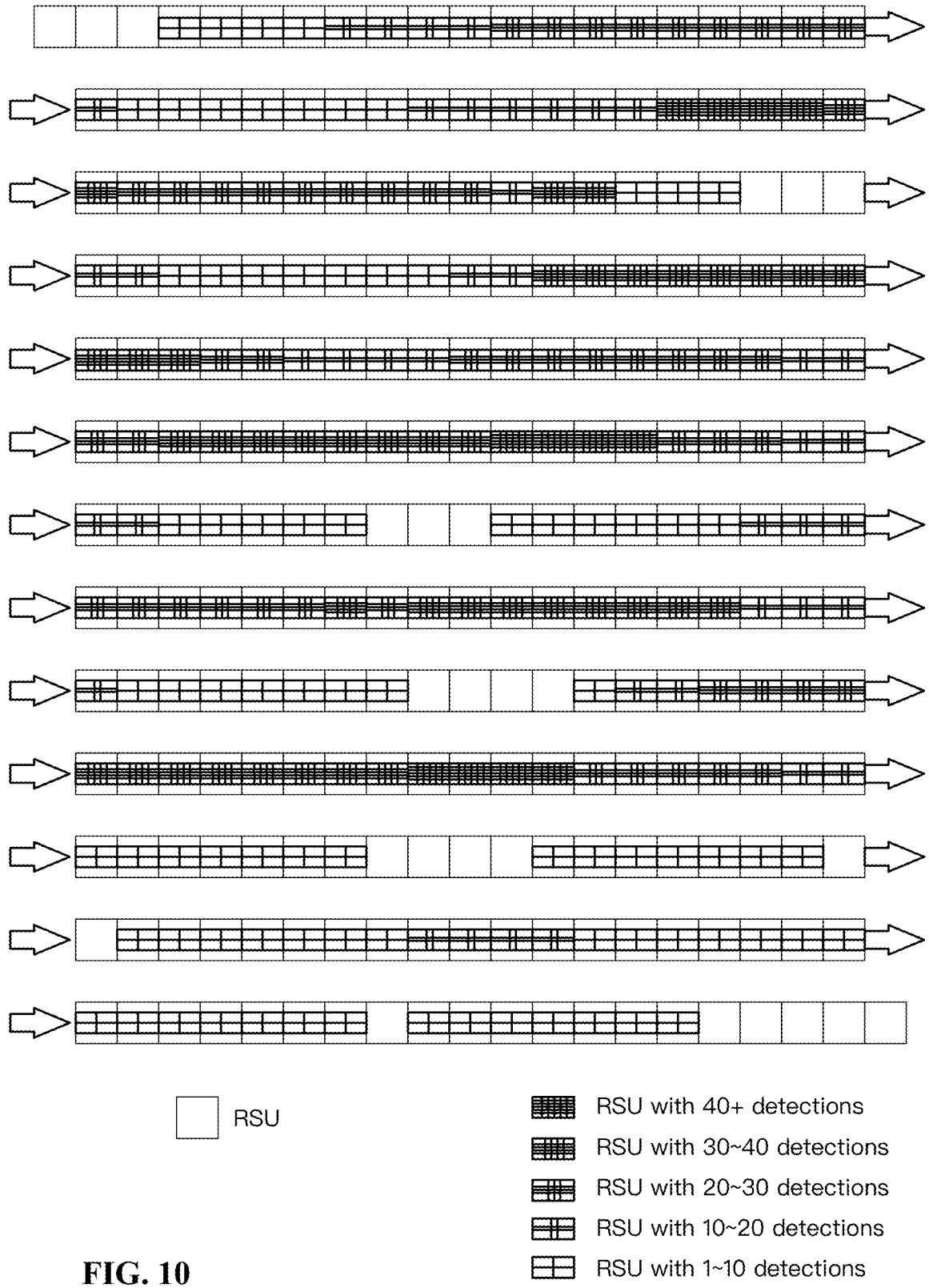
FIG. 10 is a schematic diagram of a cumulative detection distribution of a "belt"-shaped road network based on a section unit model.
Figure 11:
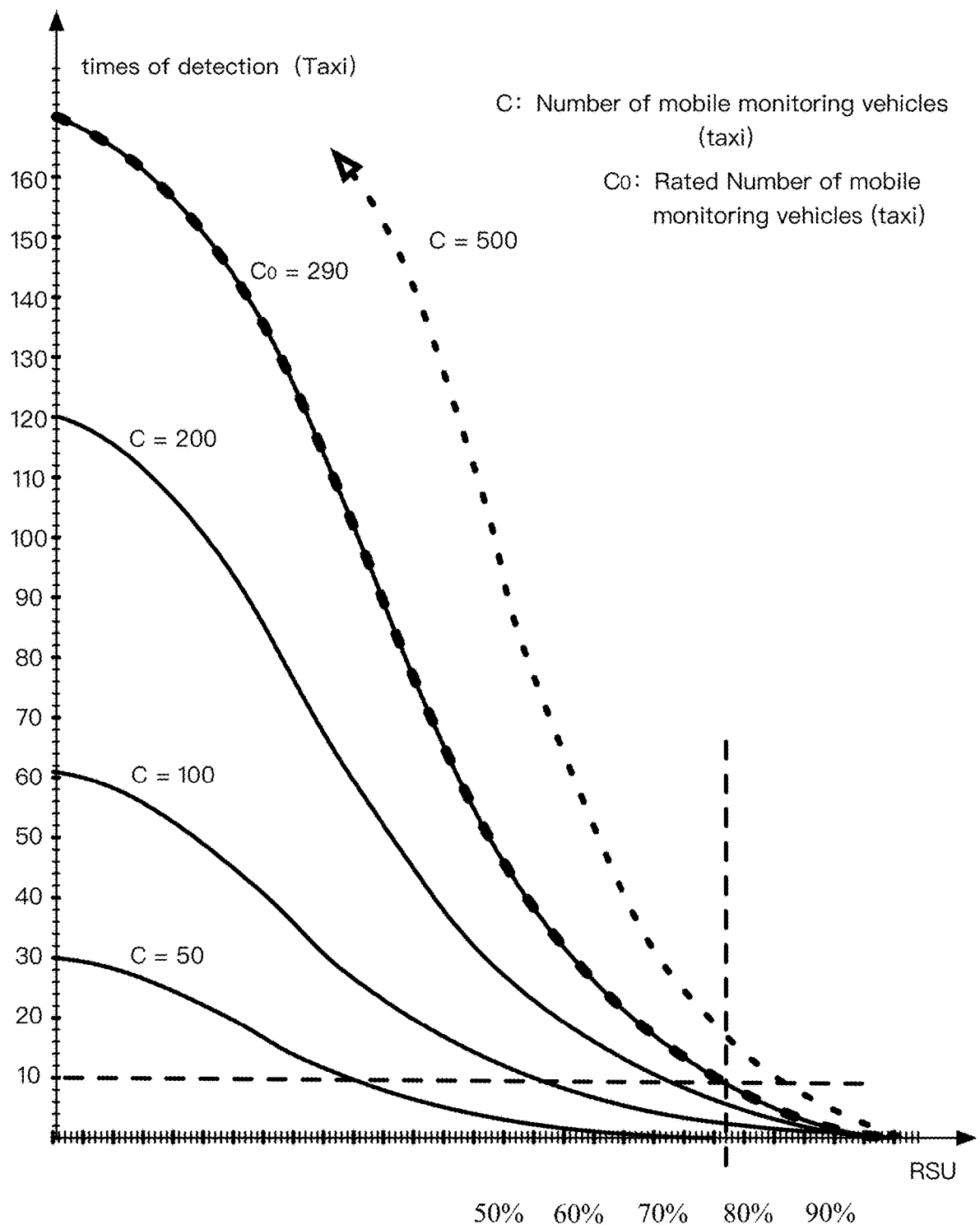
FIG. 11 depicts statistical distribution of the monitoring times (taxi) within a 24-hour period in a certain urban area by road segment unit.
Figure 12:
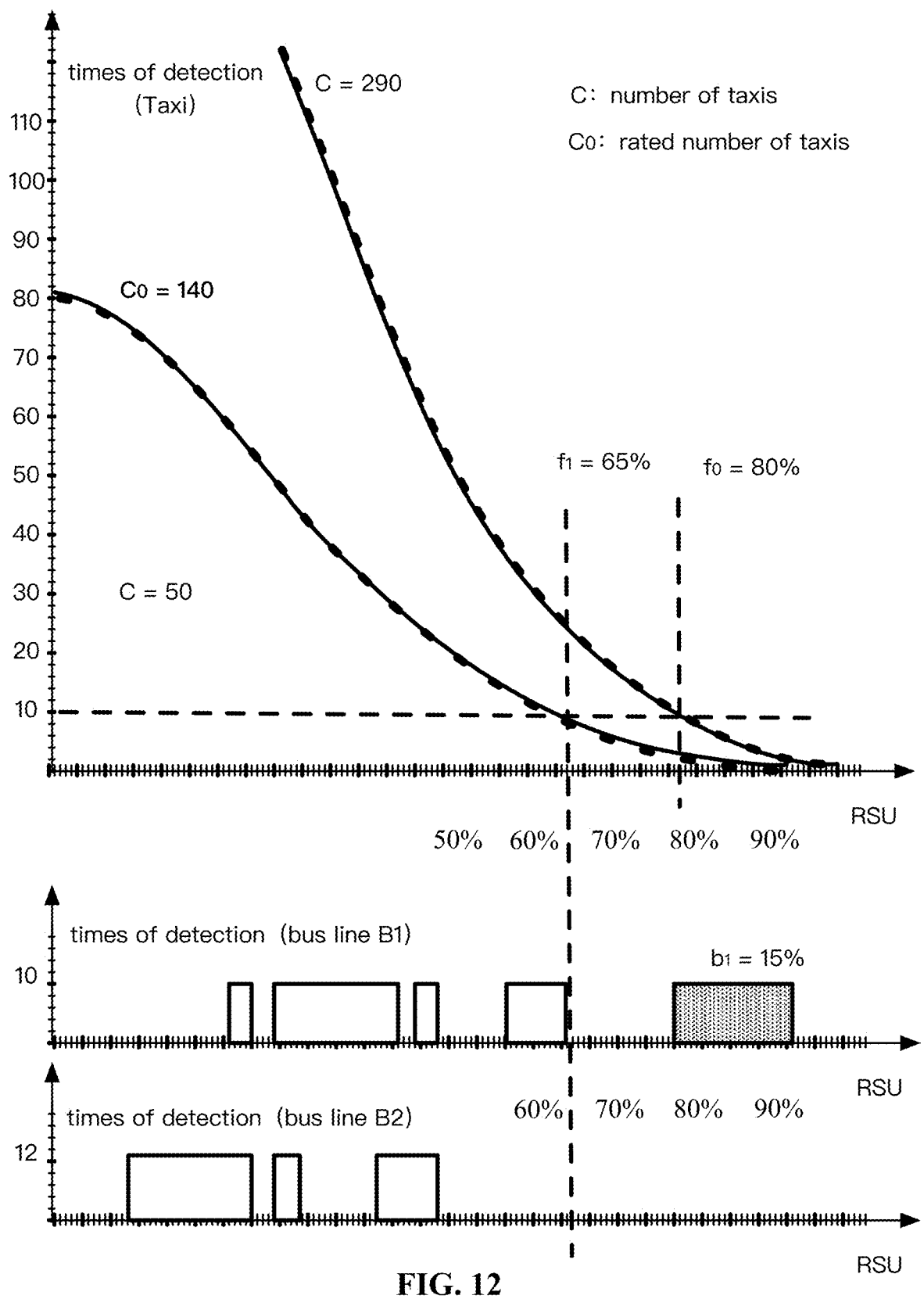
FIG. 12 is a schematic diagram of the monitoring times in the taxi and bus collaborative monitoring mode.
Figure 13:
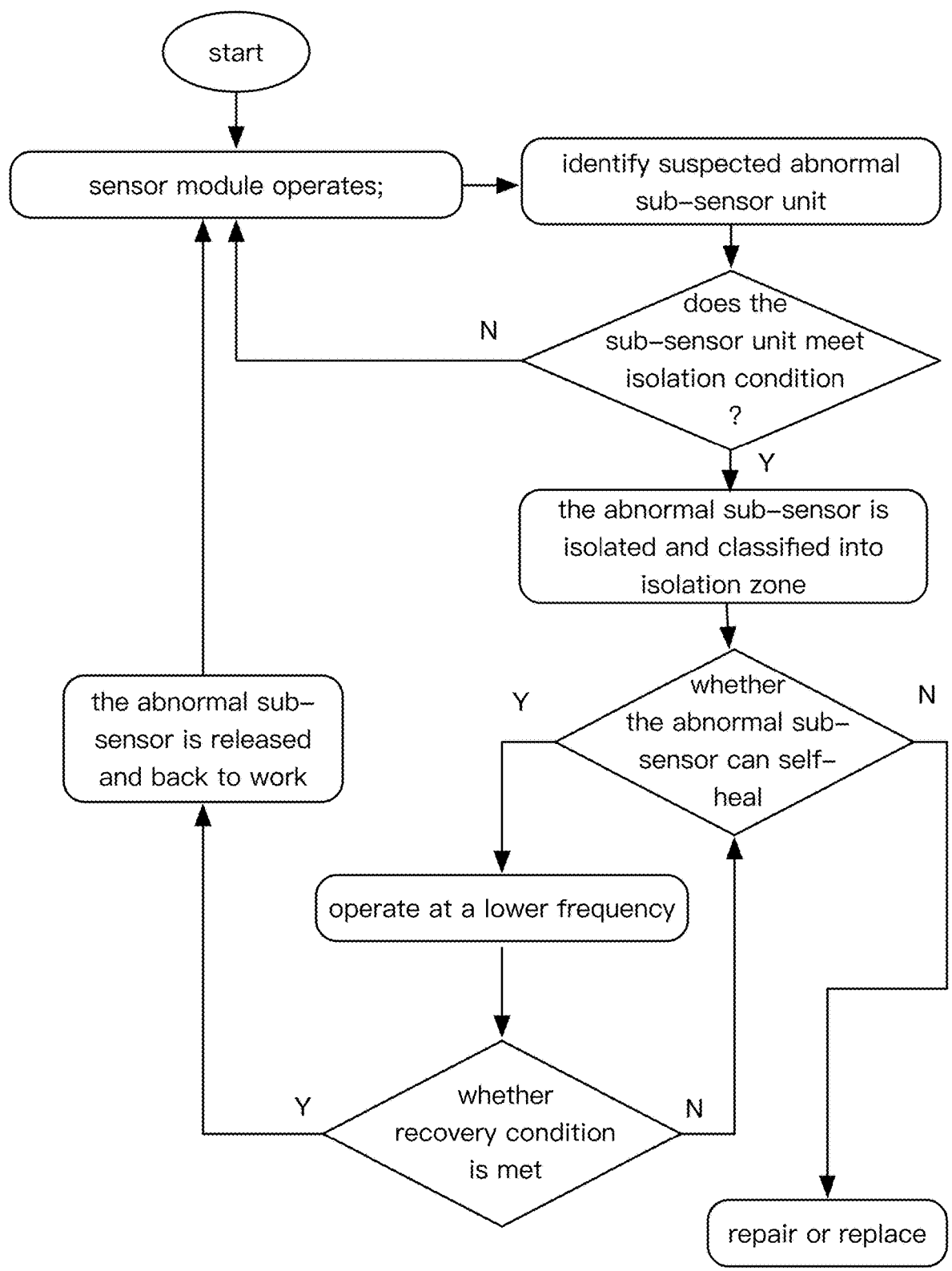
FIG. 13 is a schematic diagram of an isolation and recovery process of a high/low frequency multi-core sensor module.

Air pollutant monitoring equipment is installed on social vehicles. The monitoring equipment has concealed features, such as concealed installation inside the taxi ceiling light, the lower part of the taxi ceiling light, and the top of the bus. When traditional monitoring methods such as special monitoring vehicles and personnel conduct on-site monitoring, polluting enterprises can also timely detect and adjust the production of pollution; for fixed monitoring sites, polluting enterprises may develop corresponding countermeasures, such as changing the way of sewage outlet. In this solution, the monitoring equipment is concealed inside or under the taxi roof lights, bus roofs, etc., so that the polluted enterprises and individuals being monitored cannot know that nearby equipment is monitoring atmospheric pollutants around them, making the monitoring data objectivity has further improved. As shown in FIG. 5, the sewage company will not know that the taxi passing by the door is monitoring its pollutants.

Example 15

The disclosure is provided with an anti-tampering function for the monitoring data to ensure the reliability and accuracy of the monitoring data. The implementation mode is that the monitoring data measured by the detection module is first stored in the local storage medium of the atmospheric pollutant monitoring equipment, and the monitoring data measured by the detection module is uploaded to the monitoring center by wireless transmission, and all the original data uploaded to the monitoring center set anti-modification and anti-deletion features. The system of the monitoring center automatically or remotely retrieves the sensor's local original database and the monitoring center database for calibration. In the data transmission of air pollutant monitoring equipment and monitoring centers, you can also use the addition of a digital signature to encrypt the data transmission. Digital signature algorithms that can be used comprise RSA, ElGamal, Fiat-Shamir, Guillou-Quisquarter, Schnorr, and Ong-Schnorr-Shamir and so on.

Example 16

For social vehicles equipped with air pollutant monitoring equipment, the license plate number and the monitoring equipment SN (monitoring equipment serial number) are bound. In this way, the vehicle and equipment information can be queried and verified through the database of the monitoring center.

Example 17

Air pollutant monitoring equipment can adjust the monitoring density according to the situation of pollutants. For example, when a social vehicle equipped with air pollutant monitoring equipment passes by a certain section, the air pollutant monitoring equipment detects that the pollutant concentration exceeds the upper limit of the preset value, such as $PM_{2.5}$ value≥100 µg/m³ (also 150 µg/m³, 200 µg/m³, 250 µg/m³, etc.), the air pollutant monitoring equipment increases the frequency of air pollutant concentration detection output. For example, the value of a pollutant concentration calculated every 3 seconds is changed to a pollutant calculated every 1 second. The pollutant that triggers the increase of the detection output frequency may be other pollutants (such as nitrogen oxides, ozone, etc.) that are monitored. When the pollutant concentration is lower than the lower limit of the set value, the air pollutant monitoring equipment reduces the detection output frequency. For example, after $PM_{2.5}$≤50 µg/m³, the detection output frequency is restored to output a pollutant concentration value or longer time interval every 3 seconds.

Example 18

The air pollutant monitoring equipment can adjust the frequency of return of the detected value according to the situation of the pollutant. For example, when a social vehicle equipped with air pollutant monitoring equipment passes by a certain section, the air pollutant monitoring equipment detects that the pollutant concentration exceeds the upper limit of the preset value, such as $PM_{2.5}$ value≥100 µg/m³ (also 150 µg/m³, 200 µg/m³, 250 µg/m³, etc.), the air pollutant monitoring equipment increases the frequency of air pollutant concentration detection output. For example, the value of a pollutant concentration calculated every 3 seconds is changed to a pollutant calculated every 1 second. The pollutant that triggers the increase of the detection output frequency may be other pollutants (such as nitrogen oxides, ozone, etc.) that are monitored. When the pollutant concentration is lower than the lower limit of the set value, the air pollutant monitoring equipment reduces the detection output frequency. For example, after $PM_{2.5} \leq 50$ µg/m³, the detection output frequency is restored to output a pollutant concentration value or longer time interval every 3 seconds.

Example 19

Air pollutant monitoring equipment can adjust the monitoring density and return frequency according to the designated area or road section.

When a social vehicle equipped with atmospheric pollutant monitoring equipment enters an area or road section that needs to be monitored, the atmospheric pollutant monitoring equipment increases the output frequency of the corresponding atmospheric pollutant monitoring value. For example, the value of a pollutant concentration calculated every 3 seconds is changed to a pollutant calculated every 1 second.; when the mobile monitoring vehicle leaves the area or road section that needs to be monitored, the air pollutant monitoring device reduces the frequency of the corresponding air pollutant monitoring output, such as the output frequency returns to the level before entering the key area or road section.

When a mobile monitoring vehicle passes by an area or road section that needs to be monitored, the air pollutant monitoring device can also increase the frequency of transmitting the corresponding air pollutant monitoring data to the monitoring center, for example, the value back every 3 seconds is changed to once every 1 second; when the mobile monitoring vehicle leaves the area or road section that needs to be monitored, the air pollutant monitoring device reduces the frequency of transmitting the corresponding air pollutant monitoring data to the monitoring center, for example, transmission frequency returns to the level before entering the key area or road section.

Example 20

The example is a working mode of a video acquisition module. The video acquisition module starts working at the same time after the atmospheric pollutant monitoring equipment is started. The video content is stored on local storage media, such as TF card, SSD, hard disk, U disk, CF card. After running out of storage space, the longest video is deleted by rolling back, so that the video can be recorded all the time.

Video forensics methods:

There are three ways to retrieve videos.

First, when the monitoring center needs video content for a certain period of time, wireless instructions are used to control the video acquisition module to upload the required video to the monitoring center through wireless transmission.

Second, the mobile monitoring vehicle can be located through the monitoring center, and a video copy can be made on-site by authorized staff.

Third, when the vehicle passes a certain section, the air pollutant monitoring equipment detects that the concentration of an air pollutant exceeds the upper limit of a preset value, such as after the $PM_{2.5}$ value$\geq 200$ µg/m³ (the preset value can also be other values, The preset trigger pollutant can be other monitored pollutants such as nitrogen oxides, ozone, etc.) The air pollutant monitoring device automatically opens the upload function, and uploads related videos within a certain time before and after the pollutant preset value is exceeded to the monitoring center. For example, 5-minute video before and after the trigger is uploaded to the monitoring center.

Example 21

The example is a working mode of a video acquisition module. The video acquisition module is turned off by default. When the air pollutant monitoring device finds that the concentration of an air pollutant exceeds the upper limit of a preset value, such as after $PM_{2.5}$ value$\geq 100$ µg/m³ (the preset value can also be other values, default Triggered pollutants can be other monitored pollutants such as nitrogen oxides, ozone, etc.), and the video capture module is automatically turned on for recording. There are also three methods of video forensics. Same as in Example 19.

Example 22

This is a working mode of a video acquisition module. Air pollutant monitoring equipment has video image recognition, video image analysis, and pollution identification functions. By identifying and analyzing the video content obtained by the video acquisition module, it is possible to capture and discover the local pollution of the area passed by the mobile monitoring vehicle in time. If it is judged that there is local air pollution, upload the relevant video content within a certain period of time before and after the pollution is found to the monitoring center. For example, 5-minute video before and after the trigger is uploaded to the monitoring center. If the video uploaded to the monitoring center is judged to be polluted after being screened, the monitoring center can send pollution data and video evidence to the platform of the relevant environmental protection department or public security department. The image recognition function can set a learning mode. The data after the video forensics is manually classified by the monitoring center, and each classified video case after classification is machine-learned for scene recognition. When the artificial intelligence scene case recognition learning is completed, the detected artificial intelligence of the equipment or the artificial intelligence of the monitoring center will intelligently identify the collected video and judge the pollution.

Example 23

The example is a working mode of a video acquisition module. The monitoring center controls the air pollutant monitoring equipment mounted on social vehicles. For example, the monitoring center needs to closely observe the pollution situation in a specific area. It can instruct the vehicle to increase the calculate frequency or return frequency of the detection data if it enters the area.

For example, if data is returned every 3 seconds before entering the area, data is returned every 1 second after entering the area; a data is detected and calculated every 3 seconds before entering the area, and every 1 second after entering the area draw a data. The monitoring center can also instruct to open the camera of the video acquisition module for video forensics and real-time transmission.

It will be obvious to those skilled in the art that changes and modifications may be made, and therefore, the aim in the appended claims is to cover all such changes and modifications.

What is claimed is:

1. A method of mobile monitoring and determining a requisite number of mobile monitoring vehicles, the method focuses on a road network of an urban area, by installing air pollution detection equipment on the mobile monitoring vehicles, to monitor air quality of the urban area, the method comprising:
   1) establishing a curve model of monitoring times for the mobile monitoring vehicles, which comprises:
      1.1) decomposing the road network of the urban area into road segment units (RSUs); initializing a database of RSUs, which comprises RSU numbers, RSU locations, and RSU detection records;
      1.2) selecting at least 50 of the mobile monitoring vehicles equipped with a positioning system; recording the number of times that each mobile monitoring vehicle passes each RSU; a maximum number of times for each mobile monitoring vehicle passing any RSU within a counting period is 1;
      1.3) continuing recording for at least one week, calculating a daily average of times for each RSU; and
      1.4) creating a curve model of monitoring times for the mobile monitoring vehicles, which is a statistical distribution of monitoring times for the mobile monitoring vehicles by RSUs within 24 hours;
   2) determining a covered range and a number of scheduled detections; and
   3) finding out a requisite number ($C_0$) of the mobile monitoring vehicles, corresponding to a curve model.

2. The method of claim 1, wherein the road segment units comprise a detection device number, an accumulative time since each mobile monitoring vehicle enters each RSU, and an accumulative number of times each mobile monitoring vehicle passes each RSU; wherein an initial value of the accumulative number of times is 0.

3. The method of claim 1, wherein a length of the RSU is 100 meters or 200 meters; and a range of the counting period is 15 min, 30 min, or 1 hour.

4. The method of claim 1, wherein a value of the covered range is 70%-80%, and the number of scheduled detections is 5-10 times.

5. The method of claim 4, wherein the mobile monitoring vehicles comprise city buses, long-distance buses, taxis, earthmoving vehicles, municipal vehicles, official vehicle, ride-hailing vehicles, rental vehicles, shared vehicles, and vehicles with autonomous driving functions.

6. The method of claim 5, wherein the air pollution detection equipment comprises a control module and a detection module; wherein the detection module comprises at least one sensor unit; the sensor unit is one of the following sensors: PM1 sensor, PM2.5 sensor, PM10 sensor, PM100 sensor, Sulphur dioxide sensor, nitrogen oxide sensor, ozone sensor, carbon monoxide sensor, VOCs sensor, or TVOC sensor.

7. The method of claim 6, wherein the detection module comprises a sensor module comprising at least two sensor units of the same type; the at least two sensor units operate at a first frequency; the detection module comprises a calibration module comprising at least one sensor unit that is of the same type as the at least two sensor units of the sensor module; the sensor unit of the calibration module operates at a lower frequency than that of the sensor module.

8. The method of claim 7, wherein a ratio of operating frequencies between the at least two sensor units of the sensor module and the sensor unit of the calibration module is 2:1, 3:1, 4:1, 5:1, 6:1, 7:1, 8:1, 9:1, 10:1, 15:1, or 20:1.

9. The method of claim 8, wherein when the mobile monitoring vehicle is a taxi, the air pollution detection equipment is installed under or within a roof light of the taxi; and when the mobile monitoring vehicle is a bus, the air pollution detection equipment is installed on top of the bus.

10. The method of claim 7, wherein when the control module detects one suspected abnormal sensor unit in the sensor module and judges that the suspected abnormal sensor unit is an abnormal sensor unit, the suspected abnormal sensor unit is isolated and classified into an isolation zone.

* * * * *